US009694119B2

(12) United States Patent
Cheng et al.

(10) Patent No.: US 9,694,119 B2
(45) Date of Patent: Jul. 4, 2017

(54) SURGICAL INSTRUMENT

(71) Applicant: Gyrus ACMI, Inc., Southborough, MA (US)

(72) Inventors: Ming J. Cheng, W. Warwick, RI (US); Chee K. Teo, Alpharetta, GA (US); Kevin C. Edwards, Olive Branch, MS (US); Michael J. Bennett, Bartlett, TN (US); John P. Flynn, Collierfille, TN (US); Matthias Reif, Hamburg (DE); Phillip A. Ryan, Memphis, TN (US); Allen C. Palmer, Arlington, TN (US)

(73) Assignee: GYRUS ACMI, INC., Southborough, MA (US)

( * ) Notice: Subject to any disclaimer, the term of this patent is extended or adjusted under 35 U.S.C. 154(b) by 283 days.

(21) Appl. No.: 14/487,199

(22) Filed: Sep. 16, 2014

(65) Prior Publication Data
US 2015/0073364 A1  Mar. 12, 2015

Related U.S. Application Data

(63) Continuation-in-part of application No. 13/457,006, filed on Apr. 26, 2012, now abandoned.

(51) Int. Cl.
*A61M 1/00* (2006.01)
*A61B 17/32* (2006.01)

(52) U.S. Cl.
CPC ..... *A61M 1/0031* (2013.01); *A61B 17/32002* (2013.01); *A61B 2217/005* (2013.01);
(Continued)

(58) Field of Classification Search
CPC ............. A61B 17/32002; A61B 34/30; A61M 1/0031; A61M 1/0078; A61M 1/0064;
(Continued)

(56) References Cited

U.S. PATENT DOCUMENTS 2,006,878 A    7/1935  Bandoly
2,022,742 A   12/1935  Salemi
(Continued)

FOREIGN PATENT DOCUMENTS

JP    A0-07-000442    1/1995
JP    B2-2608424      5/1997
(Continued)

OTHER PUBLICATIONS

Jun. 3, 2013 International Search Report and Written Opinion issued in International Patent Application No. PCT/US2013/028003.

*Primary Examiner* — Richard Louis
(74) *Attorney, Agent, or Firm* — Oliff PLC

(57) ABSTRACT

A surgical instrument has a hollow tubular member, and a pressurization unit that has an outer valve portion, a pressurization device having a movable part configured to generate pressurized fluid when the movable part is moved, and an inner valve portion. The inner valve portion includes a first flow passage that is configured to fluidically connect a first port and a second port of the outer valve portion to each other when the inner valve portion is in a first position, and a second flow passage that is configured between the inner valve portion and the outer valve portion to fluidically connect the first port and a third port when the inner valve portion is in a second position. A sealing system fluidically isolates the second port and the third port from each other at any position of the inner valve portion. Pressurized fluid from the pressurization device causes the inner valve portion to move from the first position to the second position, thereby providing positive pressure to the hollow tubular member.

16 Claims, 17 Drawing Sheets

(52) U.S. Cl.
CPC ......... *A61M 1/0062* (2013.01); *A61M 1/0078* (2013.01); *A61M 1/0084* (2013.01); *A61M 2205/073* (2013.01); *A61M 2205/075* (2013.01); *A61M 2205/3334* (2013.01)

(58) Field of Classification Search
CPC .............. A61M 1/0035; A61M 39/223; A61M 2039/224; A61M 2039/242; A61M 2039/2473; A61M 2039/2486; A61M 2039/2493; A61M 1/0058; A61M 1/0062
See application file for complete search history.

(56) References Cited

U.S. PATENT DOCUMENTS

| | | | | |
|---|---|---|---|---|
| 4,036,210 A | * | 7/1977 | Campbell | A61M 16/0463 128/207.16 |
| 4,193,406 A | * | 3/1980 | Jinotti | A61M 16/0009 128/204.18 |
| 4,680,026 A | * | 7/1987 | Weightman | A61M 1/0064 433/84 |
| 5,830,214 A | * | 11/1998 | Flom | A61B 18/1482 604/33 |
| 2001/0037082 A1 | * | 11/2001 | Kamiyama | A61M 1/0064 604/43 |
| 2001/0044600 A1 | * | 11/2001 | Elkins | A61M 16/0463 604/119 |
| 2004/0019310 A1 | * | 1/2004 | Hogendijk | A61B 17/22 604/1 |
| 2004/0221904 A1 | * | 11/2004 | Usher | A61M 5/1408 137/837 |
| 2005/0182432 A1 | | 8/2005 | Fanton et al. | |
| 2005/0197645 A1 | * | 9/2005 | Karpowicz | A61M 1/0062 604/514 |
| 2006/0264995 A1 | * | 11/2006 | Fanton | A61B 17/32002 606/180 |
| 2007/0100276 A1 | | 5/2007 | Fanton et al. | |

FOREIGN PATENT DOCUMENTS

| | | |
|---|---|---|
| WO | 95/21641 | 8/1995 |
| WO | 2005/079484 | 9/2005 |
| WO | 2007/013986 | 2/2007 |

* cited by examiner

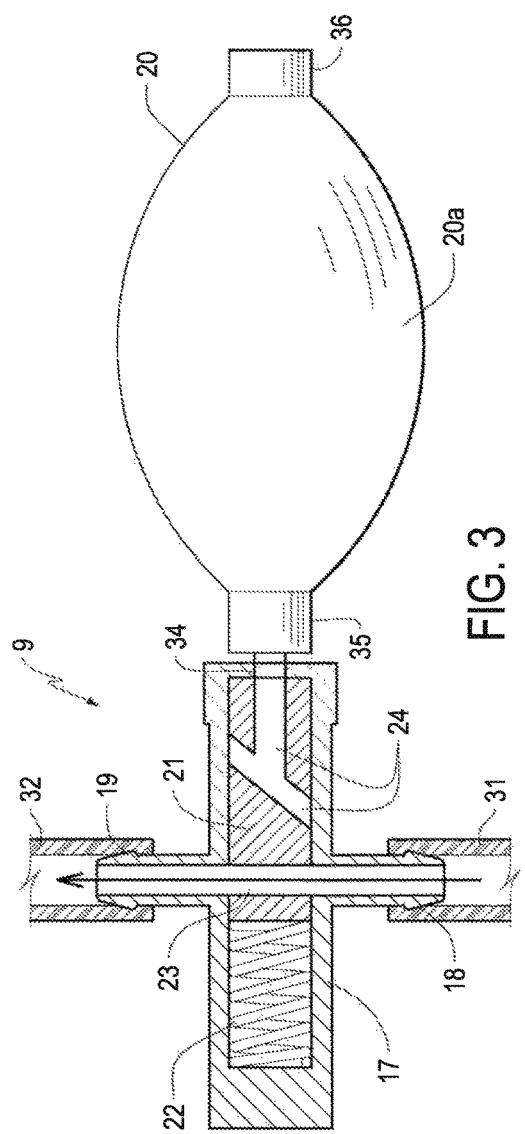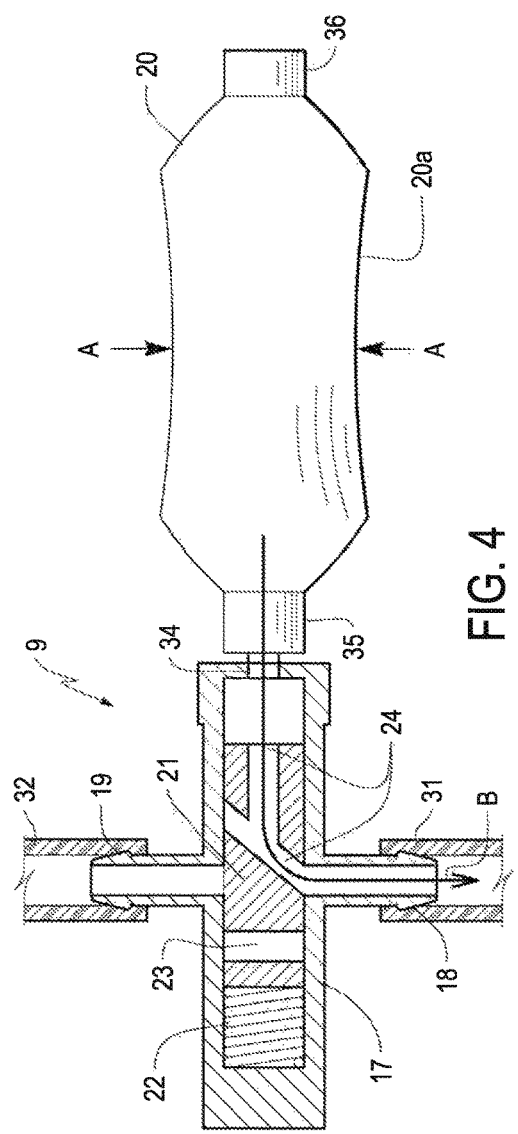

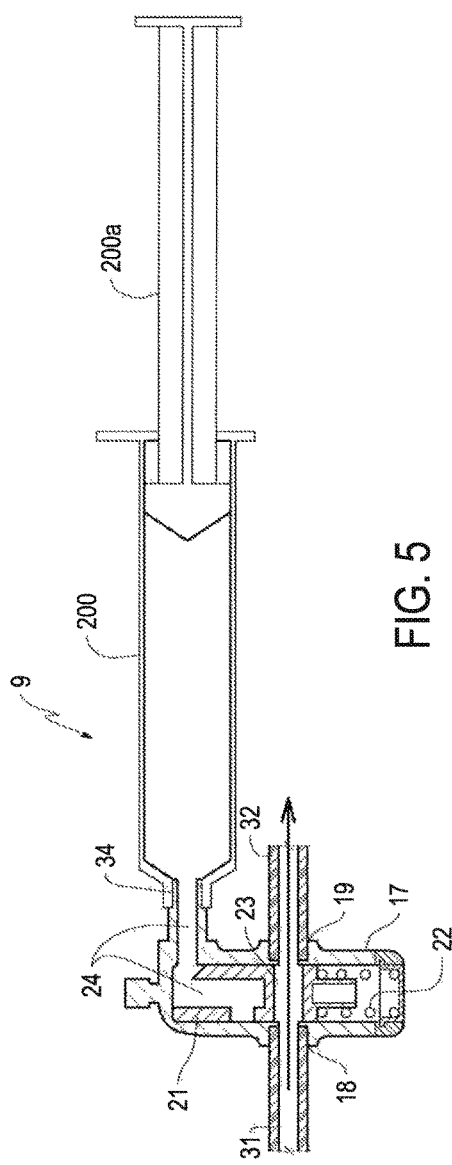
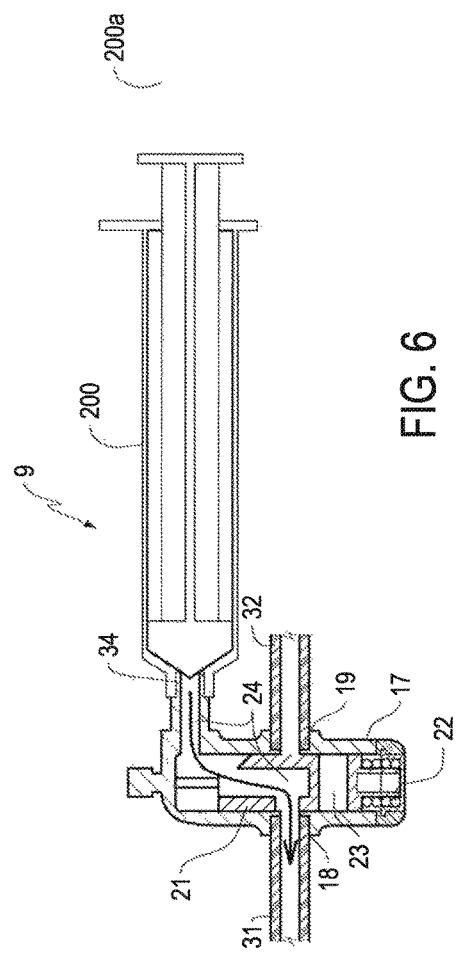
FIG. 5
FIG. 6

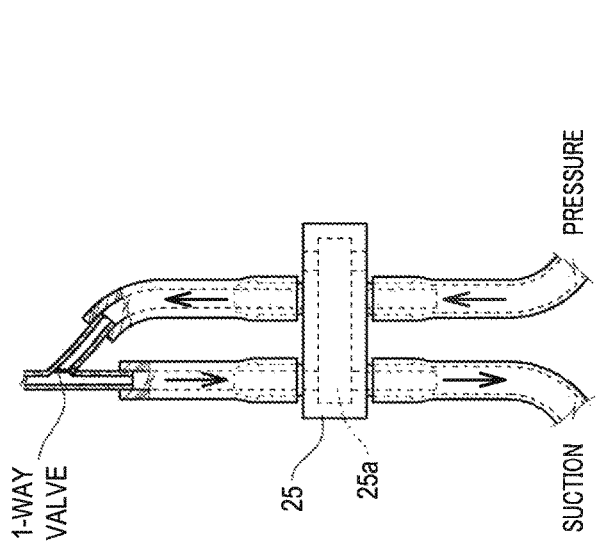
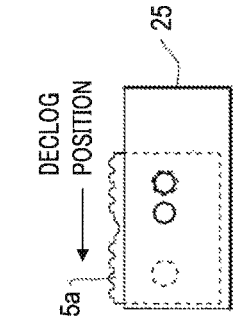
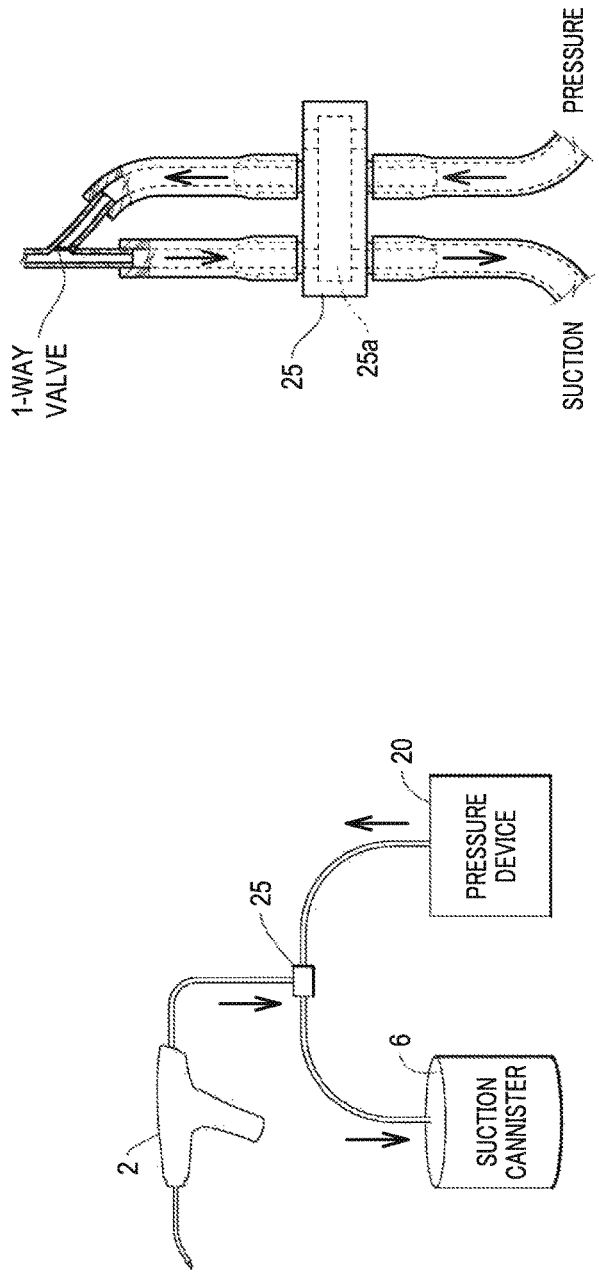
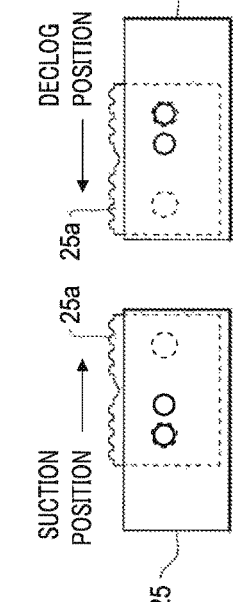
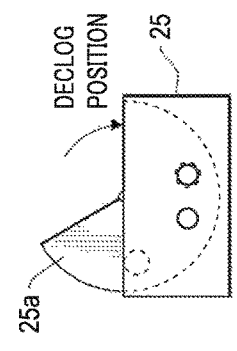
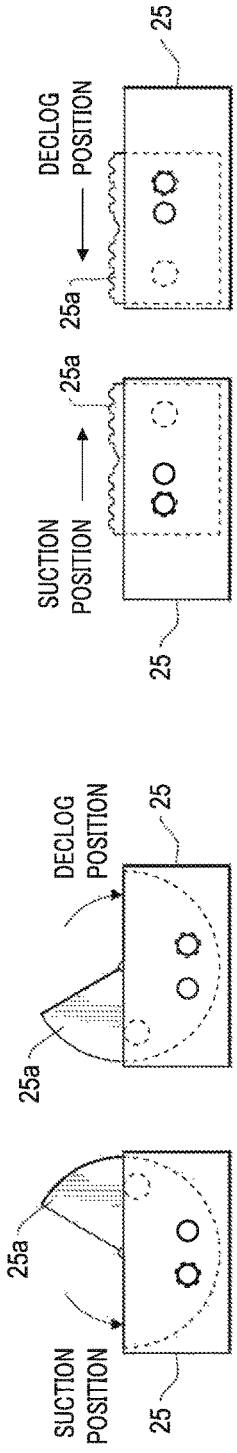

SURGICAL INSTRUMENT

This invention relates to surgical instruments that deliver fluids to and remove material from surgical sites. In particular, this invention relates to surgical instruments that, in addition to providing suction, include a positive pressure providing source to remove an obstruction such as cut biological material from the surgical instruments or irrigate the surgical instrument during a surgical procedure.

Surgical instruments used to shave, cut, resect, abrade and/or remove tissue, bone and or other bodily materials are known. Such surgical instruments can include a cutting surface, such as a rotating/reciprocating blade, disposed on an elongated inner tube that is rotated/reciprocated within an elongated outer tube having a cutting window. The inner and outer tubes together forming a surgical cutting blade. In general, the elongated outer tube includes a distal end defining an opening or cutting window that exposes the cutting surface of the inner tube (at the distal end of the inner tube) to tissue, bone and/or any other bodily materials.

Once the tissue, bone and/or any other bodily materials are cut, it is necessary to remove them from the surgical site. This is typically accomplished through an inner lumen provided in the surgical instrument that is connected to a suction source. Existing surgical instruments utilize a one-way suction line to aspirate tissue from the surgical site. It is often the case that the tissue forms a clog in the aspiration pathway (most often in the distal end of the surgical instrument). One way to remove the clog is for the person using the surgical instrument to remove the instrument from the surgical site and insert a stylet into the cutting window to force the clog through the cutting portion and into the inner lumen to be aspirated. However, this is often a time-consuming and tedious process, particularly over the course of a surgical procedure in which the surgeon may have to remove multiple clogs. Furthermore, removing and reinserting the surgical instrument is traumatic to the surgical site.

U.S. Patent Application Publication No. 2006/0264995 A1 discloses various embodiments in which, when a clog is detected in a surgical cutting instrument, flow in aspiration tubing is interrupted and the aspiration tubing is compressed such that a positive pressure is provided to unclog the surgical cutting instrument (see FIGS. 2A-8). U.S. Patent Application Publication No. 2006/0264995 A1 also discloses embodiments in which a valve cuts off suction to the surgical cutting instrument and then a separate actuation of a means for flushing causes pressurized fluid to be provided to unclog the surgical cutting instrument (see FIGS. 18A-21B). However, the various embodiments disclosed in U.S. Patent Application Publication No. 2006/0264995 A1 can be either difficult to use in practice or are inadequate to fully clear a clog quickly and efficiently.

Therefore, in view of the above-mentioned problems associated with clearing clogs from a surgical instrument, it is desirable to develop ways of clearing clogs quickly and efficiently.

SUMMARY

In view of the above, it is desirable to provide a surgical instrument having a mechanism to remove a clog using a fluid (air or liquid) to create a back pressure that will blow out the debris and clear a pathway in the surgical instrument. Preferred embodiments are capable of removing clogs by one action of the user (e.g., by pushing a button or actuating a pressurization mechanism that results in providing pressure and changing a pathway at one time) and through a relatively simple structure.

According to one embodiment, the surgical instrument includes a hollow tubular member having a cutting blade disposed on a distal end thereof. A handpiece is connected to a proximal end of the hollow tubular member and has a suction passage that connects to the hollow tubular member. A suction pump is configured to aspirate tissue that is cut by the cutting blade. A pressurization unit is provided between the suction passage and the suction pump. The pressurization unit includes an outer valve portion having a first port that connects to the suction passage and a second port that connects to the suction pump, and a pressurization device that is connected to the outer valve portion. The pressurization device has a movable part that is configured to generate pressurized fluid when the movable part is moved. An inner valve portion is slidably provided within the outer valve portion and is configured to move from a first position to a second position. The inner valve portion includes a first flow passage configured to connect the first port and the second port of the outer valve portion to each other when the inner valve portion is in the first position, and a second flow passage configured to connect the first port of the outer valve portion to the pressurization device when the inner valve portion is in the second position. The pressurization unit is configured such that the pressurized fluid from the pressurization device causes the inner valve portion to move from the first position to the second position, thereby providing positive pressure to the hollow tubular member.

The inner valve portion may be biased towards the first position by a spring that provides a biasing force to the inner valve portion. The spring may be secured to the inner valve portion and the outer valve portion and the spring may be fluidically isolated from the first flow passage and the second flow passage. The pressurization device may be a compressed air cylinder, a manually compressible syringe or a manually compressible inflation bulb. The movable part may be manually actuated to cause the inner valve portion to move from the first position to the second position.

A method for clearing an obstruction from a surgical instrument includes providing a hollow tubular member having a cutting blade disposed on a distal end thereof, and providing a handpiece connected to a proximal end of the hollow tubular member and having a suction passage that connects to the hollow tubular member. The method also includes providing a suction pump that is configured to aspirate tissue that is cut by the cutting blade, and providing a pressurization unit between the suction passage and the suction pump. The pressurization unit includes an outer valve portion having a first port that connects to the suction passage and a second port that connects to the suction pump, and a pressurization device connected to the outer valve portion. The pressurization device has a movable part configured to generate pressurized fluid when the movable part is moved, and an inner valve portion slidably provided within the outer valve portion and configured to move from a first position to a second position. The inner valve portion includes a first flow passage configured to connect the first port and the second port of the outer valve portion to each other when the inner valve portion is in the first position; and a second flow passage that is configured to connect the first port of the outer valve portion to the pressurization device when the inner valve portion is in the second position. The method further includes clearing an obstruction from the surgical instrument by actuating the movable part, which causes the pressurized fluid from the pressurization device to move the inner valve portion from the first position to the second position thereby providing positive pressure to the hollow tubular member.

The method may include manually operating the movable part to switch the inner valve portion from the first position to the second position.

Another embodiment relates to a microdebrider having a hollow tubular member that includes a rotatable inner tube having a cutting surface at a distal end; and an outer tube that includes a cutting window at a distal end. The rotatable inner tube is received within the outer tube so as to align the cutting surface of the rotatable inner tube with the cutting window of the outer tube. A handpiece is connected to a proximal end of the hollow tubular member and has a suction passage that connects to an inner passage of the rotatable inner tube. A suction pump is provided and is configured to aspirate tissue that is cut by the cutting surface. A pressurization unit is provided between the suction passage and the suction pump. The pressurization unit includes an outer valve portion having a first port that connects to the suction passage and a second port that connects to the suction pump, and a manually compressible inflation bulb connected to the outer valve portion. The inflation bulb is compressible so as to generate pressurized gas. An inner valve portion is provided within the outer valve portion and is configured to linearly slide from a first position to a second position. The inner valve portion includes a first flow passage configured to connect the first port and the second port of the outer valve portion to each other when the inner valve portion is in the first position, and a second flow passage configured to connect the first port of the outer valve portion to the inflation bulb when the inner valve portion is in the second position. The inner valve portion is biased toward the first position by a spring. The pressurization unit is configured such that the pressurized gas from compressing the inflation bulb causes the inner valve portion to move against a bias force of the spring and move from the first position to the second position, thereby providing positive pressure to the hollow tubular member to clear an obstruction.

According to another embodiment, the surgical instrument includes a hollow tubular member having a distal end. A handpiece is connected to a proximal end of the hollow tubular member and has a suction passage that connects to the hollow tubular member. A suction pump is configured to create suction at the distal end of the tubular member. A pressurization unit is provided between the suction passage and the suction pump. The pressurization unit includes an outer valve portion having a first port that connects to the suction. passage, a second port that connects to the suction pump, and a third port that connects to a pressurization device. The pressurization device has a movable part that is configured to generate pressurized fluid when the movable part is moved. An inner valve portion is slidably provided within the outer valve portion and is configured to move from a first position to a second position. The inner valve portion includes a first flow passage configured to connect the first port and the second port of the outer valve portion to each other when the inner valve portion is in the first position. The inner valve portion is configured to create a second flow passage configured to pass between the exterior of the inner valve portion and the interior of the outer valve portion when the inner valve portion is in the second position. The pressurization unit is configured such that the pressurized fluid from the pressurization device causes the inner valve portion to move from the first position to the second position, thereby providing positive pressure to the hollow tubular member.

The surgical instrument may have a sealing system that fluidically seals the second port from the third port when the inner valve member is in the first position, when the inner valve member is in the second position, or when the inner valve member is in any position between the first position and second position. The sealing system may include first and second compliable sealing members. The inner valve portion may be configured to move from the first position to the second position in a direction of slidable movement that is linear. The sealing system may include a first groove and a second groove disposed around the periphery of the inner valve portion. The first groove and second groove may be inclined at a first angle and a second angle to a plane that is perpendicular to the direction of slidable movement of the inner valve portion, respectively. The first groove and second groove may be configured to accept the first and second compliable seal members, respectively.

According to another embodiment, the surgical instrument may include a hollow tubular member having a distal end. A suction passage connects to the hollow tubular member. A suction pump is configured to produce suction at the distal end of the tubular member. A pressurization unit is provided between the suction passage and the suction pump. The pressurization unit includes an outer valve portion having a first port that connects to the suction passage, a second port that connects to the suction pump, and a third port that connects to a pressurization device. The pressurization device has a movable part that is configured to generate pressurized fluid when the movable part is moved. An inner valve portion is slidably provided within the outer valve portion and is configured to move from a first position to a second position. The inner valve portion includes a first flow passage that is configured to connect the first port and the second port of the outer valve portion to each other when the inner valve portion is in the first position. The inner valve portion includes a second flow passage that is configured to connect the first port and the third port of the outer valve portion to each other when the inner valve portion is in the second position. The pressurization unit includes a first compliable seal member configured to produce a fluidic seal between the second port and the third port when the inner valve portion is in the first position, and a second compliable seal member configured to produce a fluidic seal between the second port and the third port when the inner valve portion is in the second position.

The first port and the second port may be in line with each other. The first flow passage may be a straight bore through the inner valve portion. The first flow passage may be configured to be in line with the first port and the second port when the inner valve portion is in the first position According to another embodiment the surgical instrument may include a hollow tubular member having a distal end. A handpiece is connected to a proximal end of the hollow tubular member and has a suction passage in fluid connection with the hollow tubular member. A suction pump is configured to produce suction at the distal end of the tubular member. A pressurization unit is provided between the suction passage and the suction pump. The pressurization unit includes an outer valve portion having a first port that connects to the suction passage, a second port that connects to the suction pump, and a third port connected to a pressurization device. The first port and the second port may be in line with each other. The pressurization device has a movable part that is configured to generate pressurized fluid when the movable part is moved. An inner valve portion is slidably provided within the outer valve portion and is configured to move from a first position to a second position. The inner valve portion includes a first flow passage that is configured to pass through the inner valve portion and connect the first port and the second port of the outer valve portion to each other when the inner valve portion is in the first position. The first flow passage may be a straight bore through the inner valve portion that is configured to be in line with the first port and the second port When the inner valve portion is in the first position. A second flow passage is configured to pass between the exterior of the inner valve portion and the interior of the outer valve portion to connect the first port and the third port of the outer valve portion to each other device when the inner valve portion is in the second position. A seal system fluidically seals the second port from the third port when the inner valve member is in the first position, when the inner valve member is in the second position, and in any position between the first position and the second position. The pressurization unit is configured such that the pressurized fluid from the pressurization device causes the inner valve portion to move from the first position to the second position, thereby providing positive pressure to the hollow tubular member.

The pressurization unit may able be used to provide irrigation and suction to other surgical devices that may require both irrigation and suction. One such device may be an endoscope cleaning sheath.

BRIEF DESCRIPTION THE DRAWINGS

Various exemplary embodiments of the disclosed surgical instrument will be described in detail with reference to the following drawings in which:

FIG. 3 illustrates a pressurization unit in a suction position according to a first embodiment;

FIG. 4 illustrates the pressurization unit according to the first embodiment while in a de-clog position;

FIG. 5 illustrates a pressurization unit in a suction position according to a second embodiment;

FIG. 6 illustrates the pressurization unit according to the second embodiment while in a de-clog position;

FIG. 13 illustrates an embodiment having a switch unit other than a trumpet valve;

FIG. 14 illustrates another embodiment having a switch unit other than a trumpet valve;

FIGS. 15a-15d illustrate various types of switches including a rocker switch and a sliding switch;

Figure 20A:
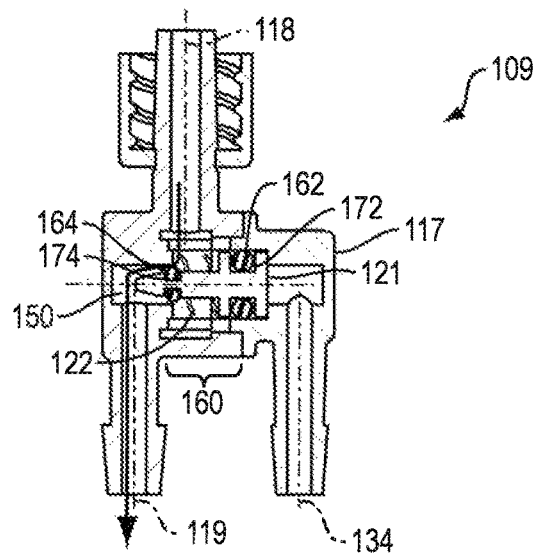
Figure 20B:
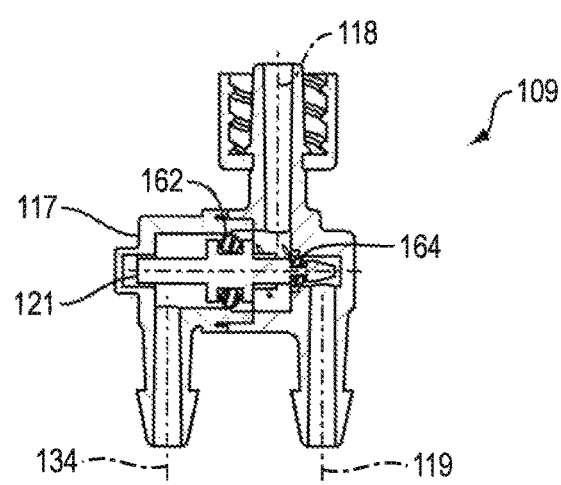
Figure 20C:
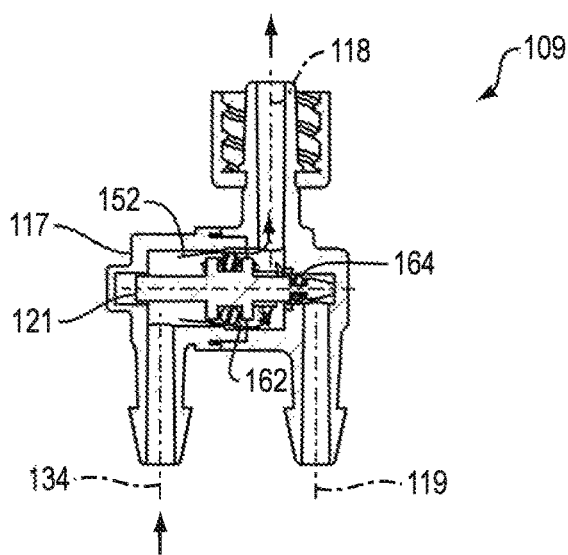

FIG. 20a-c illustrates a pressurization unit according to a seventh embodiment.

Figure 21A:
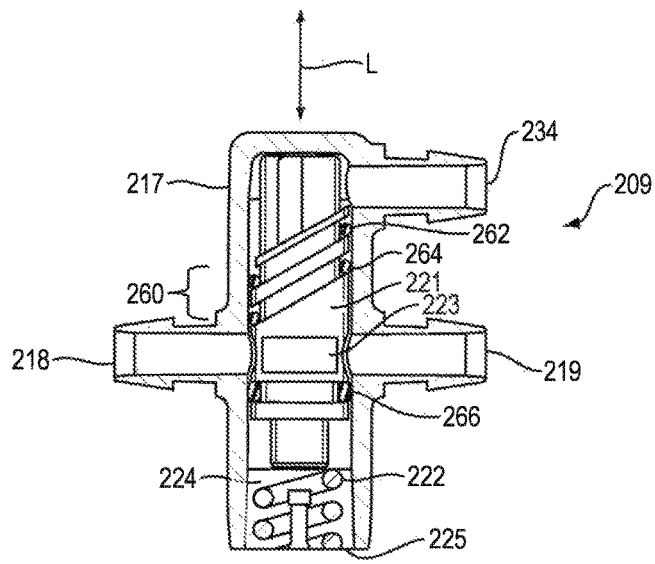
Figure 21B:
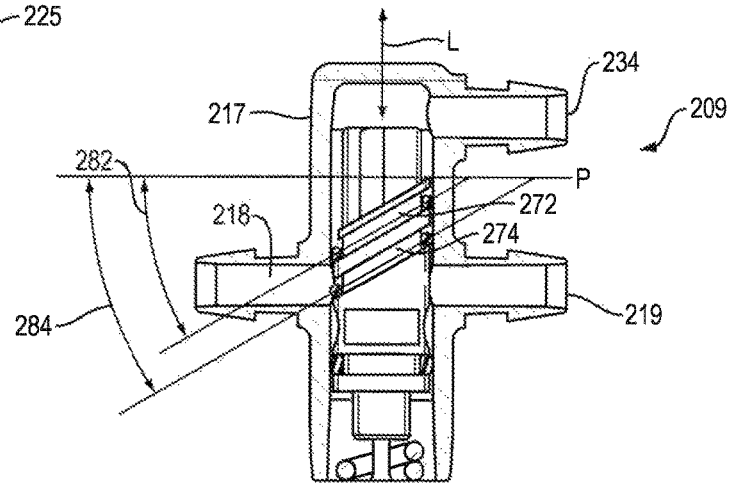
Figure 21C:
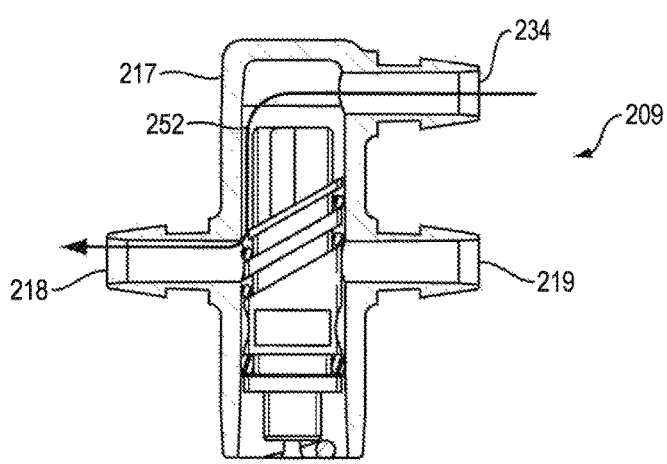

FIG. 21a-c illustrates a pressurization unit according to an eighth embodiment.

Figure 22A:
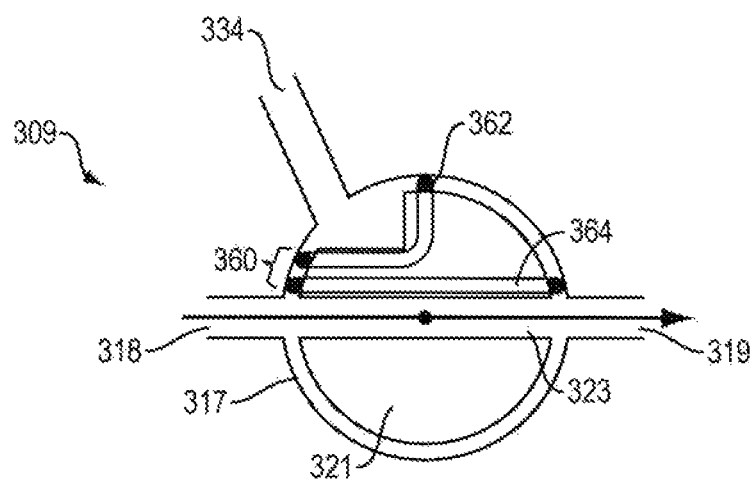
Figure 22B:
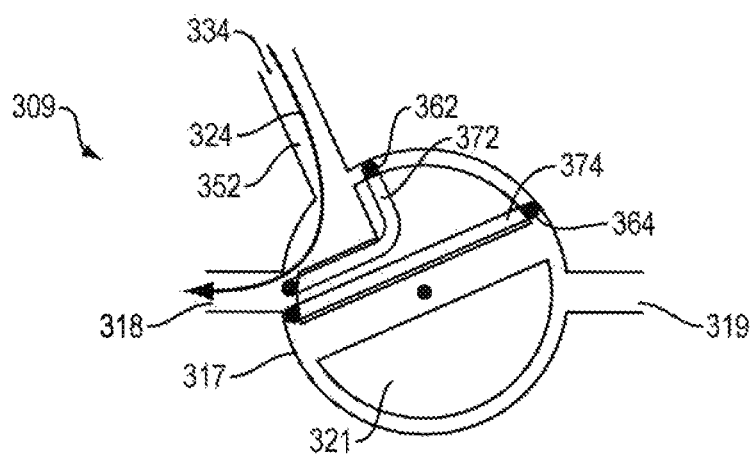

FIG. 22a-b illustrates a pressurization unit according to a ninth embodiment.

DETAILED DESCRIPTION OF EMBODIMENTS

Figure 1:
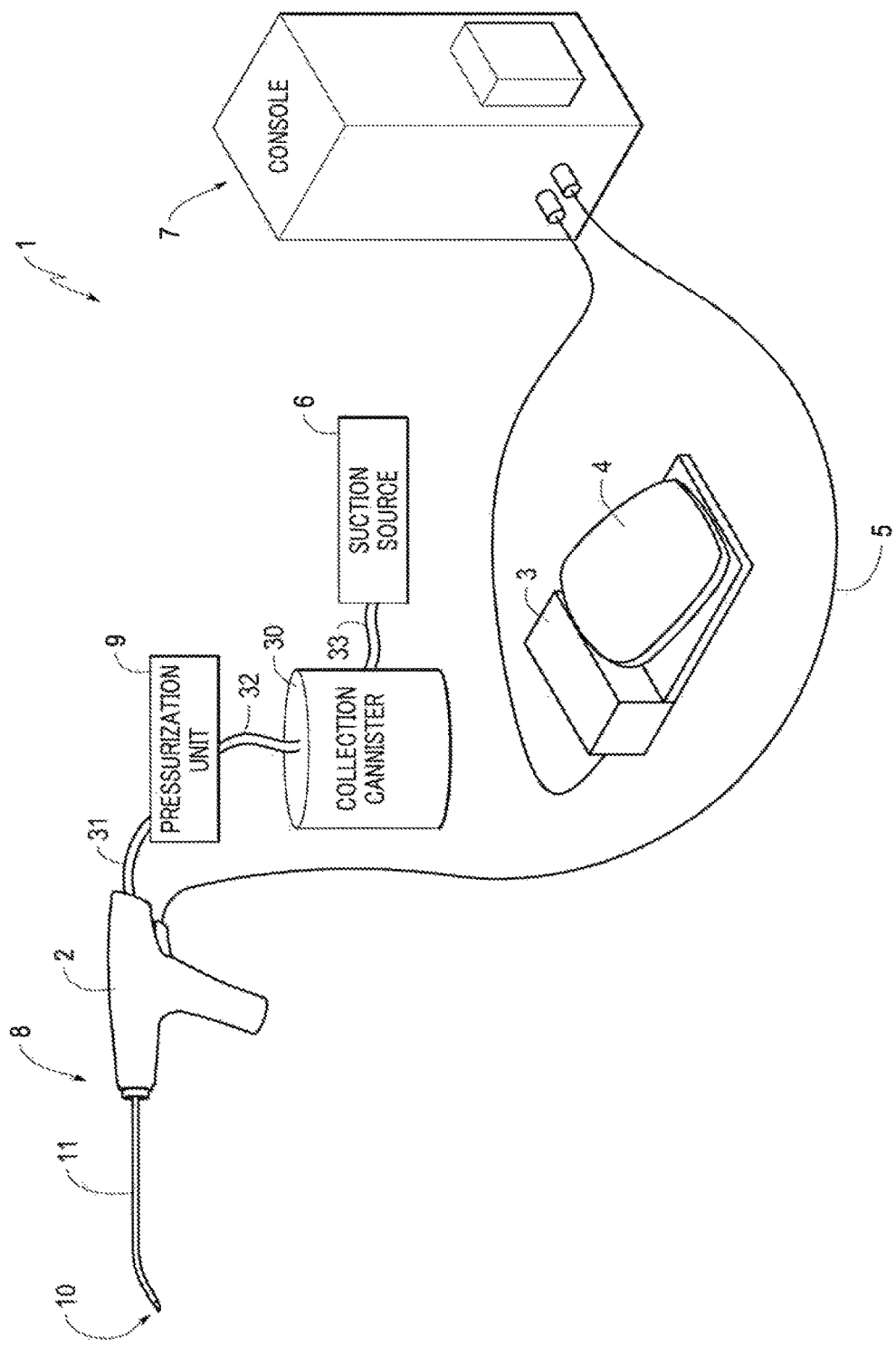
FIG. 1 illustrates a perspective view of a powered surgical tool system that incorporates a controller, a power source, a suction source, a pressurization unit and a surgical instrument having a handpiece.

FIG. 1 is a schematic of a powered surgical tool system 1. The powered surgical tool system 1 includes a footswitch 3 (with pedal 4), a suction source 6, a console 7, a pressurization unit 9 and a surgical instrument 8 having a handpiece 2. The console 7 contains a power supply for the handpiece 2. A handpiece power cable 5 between the handpiece 2 and the console 7 is the electrical connection that powers a drive motor inside the handpiece 2. A power cord from a wall outlet plugs into the console 7 to power it. The suction source 6 may be a suction pump or any other suction providing source. The handpiece 2 is connected, at its distal end, to a surgical tool 10, which includes a hollow tubular member 11. The surgical tool 10 may be a microdebrider that includes a cutting blade 12 (see FIG. 2) at its distal end that is used to cut, shave, remove, resect and/or abrade tissue, bone and/or other bodily materials. As seen in FIG. 1, the pressurization unit 9 may be provided between the suction source 6 and the handpiece 2.

A collection canister 30 is provided between the suction source 6 and the pressurization unit 9. The pressurization unit 9 is connected to the handpiece 2 by a first suction tube 31, the collection canister 30 is connected to the pressurization unit 9 by a second suction tube 32, and the collection canister 30 is connected to the suction source 6 by a third suction tube 33. Preferably the second suction tube 32 is longer than the first suction tube 31. For example, the first suction tube 31 may be approximately 18 inches such that the pressurization unit 9 is in the sterile field for actuation by the surgeon and/or a surgical assistant. On the other hand, the second suction tube 32 may be approximately 10 feet in length such that the end of the suction tubing can easily reach the collection canister 30.

Figure 2:
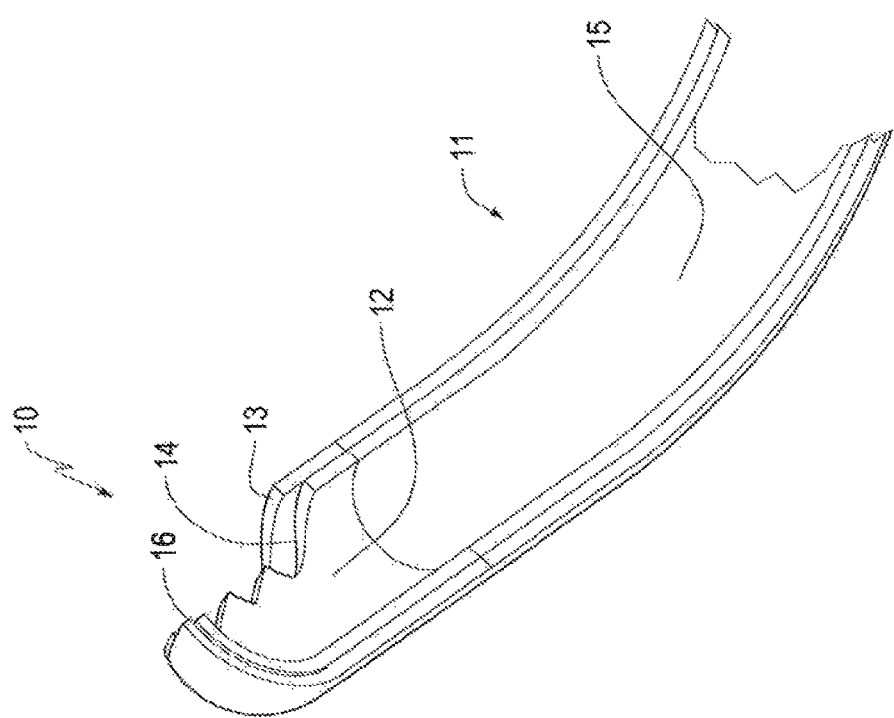
FIG. 2 illustrates a distal end portion of the surgical instrument including a cutting portion.

FIG. 2 illustrates a cross-sectional view of a distal end of the surgical tool 10 in Which an inner tube 12 is co-axially disposed within an outer tube 13. The inner tube 12 includes a suction passage 15 that extends the length of the inner tube 12. The inner tube 12 also includes a cutting blade 14 while the outer tube 13 includes a cutting window 16 at a distal end. The inner tube 12 is co-axially disposed within the outer tube 13 such that the cutting blade 14 is exposed at the cutting window 16. The cutting blade 14 disposed within the cutting window 16 form a cutting portion, which cuts by rotating/reciprocating the inner tube 12 within the outer tube 13. Suction is provided through the suction passage 15 to remove tissue, bone and/or any other bodily materials from the surgical site and to convey the removed material into the collection canister 30. Alternatively, pressurized fluid can be provided through the suction passage 15 to clear, if necessary, a clog in the suction passage 15 or at a distal end of the surgical tool 10.

FIG. 3 illustrates the pressurization unit 9 according to a first embodiment. In the embodiment illustrated in FIG. 3, the pressurization unit 9 includes an outer valve portion 17 that has a first port 18 that connects to the handpiece 2, and ultimately to the suction passage 15 of the inner tube 12, and a second port 19 that connects to the suction source 6 via the collection canister 30. The pressurization unit 9 also includes a pressurization device 20 that is connected to a third port 34 of the outer valve portion 17. In the embodiment illustrated in FIG. 3, the pressurization device 20 is a manually compressible inflation bulb. The pressurization device 20 has a movable control part 20a, which is the compressible part of the manually compressible inflation bulb.

An inner valve portion 21 is slidably provided within the outer valve portion 17 so as to be able to move from a first position to a second position. The inner valve portion 21 is biased towards the first position (illustrated in FIG. 3) preferably by means of a spring 22. However, the inner valve portion 21 may be biased towards the first position by a rubber gasket instead of a spring or by any other suitable biasing means. The inner valve portion 21 includes a first flow passage 23 and a second flow passage 24.

When the inner valve portion 21 is in the first position (illustrated in FIG. 3), suction is provided to the hollow tubular member 11 via the first port 18, the first flow passage 23 and the second port 19, which connects to the suction source 6 via the collection canister 30.

As seen in FIG. 4, when the movable part 20a of the pressurization device 20 is compressed in the direction of arrows A, positive pressure emitted from the inflation bulb into a passage at the third port 34 (the right end of the outer valve portion 17 in FIGS. 3 and 4) causes the inner valve portion 21 to slide in a direction toward pressure flow (leftward in FIGS. 3 and 4) within the outer valve portion 17 against the biasing force of the spring 22 to move the inner valve portion 21 from the first position to the second position. This causes the positive pressure emitted from the inflation bulb to pass in the direction of arrow B into the second flow passage 24, out the first port 18 and to the hollow tubular member 11, thereby causing a clog to be cleared from the hollow tubular member 11. The clog may also be cleared from any other portion of the surgical tool 10 between the pressurization unit 9 and the cutting window 16 (e.g. in the first suction tube 31). The positive pressure provided by compressing the pressurization device 20a can be any type of fluid such as either a gas or a liquid. The inflation bulb preferably includes a first one-way valve 35 (e.g., a flapper valve) at its exit aperture (on the left side in FIGS. 3 and 4) so that when the inflation bulb is squeezed, the pressurized fluid moves out of the inflation bulb and into the outer valve portion 17. The inflation bulb also preferably has a second one-way valve 36 (e.g., a flapper valve) at its entrance aperture (on the right side of the inflation bulb in FIGS. 3 and 4) so that when the bulb is released, fresh fluid enters (and fills) the bulb from the right side. Accordingly, fluid from the surgical site will not enter the inflation bulb, protecting the inflation bulb from contamination.

FIG. 5 illustrates a second embodiment, which is similar to the first embodiment except that the pressurization device 20 is a syringe 200 instead of a manually compressible inflation bulb. The syringe 200 includes a movable part (plunger) 200a that, when depressed in the direction of arrow C (see FIG. 6), causes the inner valve portion 21 to move from the first position to the second position and, as a result, causes positive pressure to be provided to clear a clog. Similar to the embodiment illustrated in FIG. 3, preferably a spring 22 biases the inner valve portion 21 towards the first position. However, negative pressure created by retracting the plunger 200a could be used to move the inner valve portion 21 towards the first position. The syringe 200 may also be configured to be removed and filled with fluid prior to being reattached to the outer valve portion 17.

Figure 7:
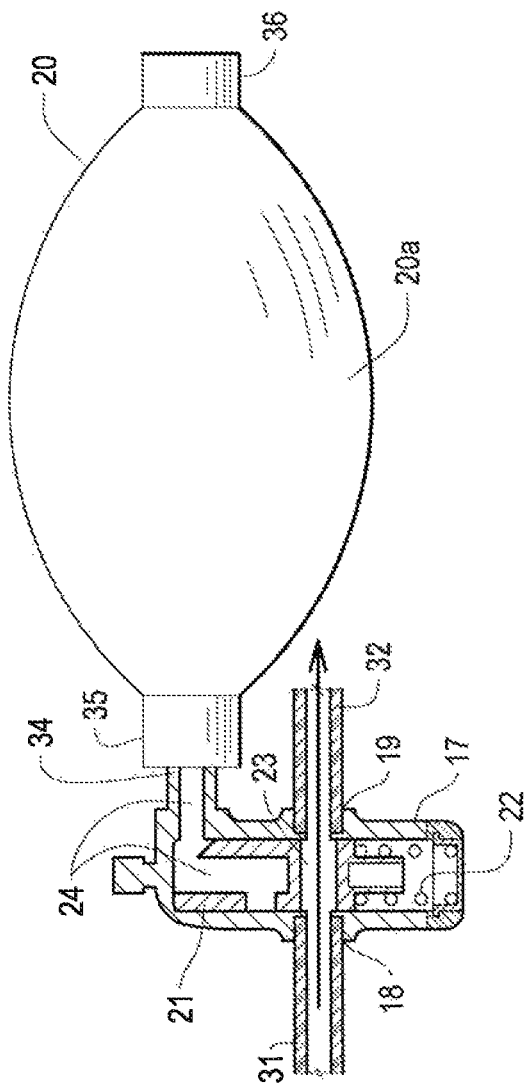
FIG. 7 illustrates a pressurization unit in a suction position according to a third embodiment.

FIG. 7 illustrates a third embodiment in which the outer valve portion 17 and inner valve portion 21 are similar to that illustrated in FIGS. 5 and 6, but an inflation bulb is provided as the pressurization device 20 instead of a syringe. The inflation bulb functions in the same manner as described with respect to the first embodiment.

Instead of using an inflation bulb or a syringe, a compressed air cylinder could be used as the pressurization device. Rotating the compressed air cylinder (for example by 90 degrees) would cause pressurized gas to be emitted from the cylinder into the outer valve portion 17 to cause the inner valve portion 21 to move from the first (suction) position to the second (de-clog) position. Rotating the cylinder back to its original position would stop the flow of pressurized gas and return the inner valve portion 21 to the suction position. A stopcock, push-button, or other manually actuated 2-position valve could be incorporated between the air cylinder and the pressurization device to control flow of gas from the air cylinder.

Figure 8:
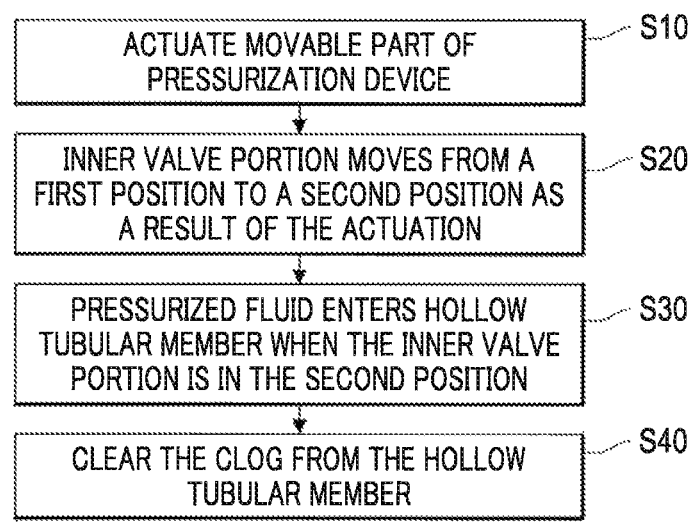
FIG. 8 illustrates a flow chart of a de-clog process.

FIG. 8 is a flow chart illustrating a process in which a clog may be cleared from, for example, the hollow tubular member 11, with reference being had to the first embodiment. In step S10, the movable part 20a of the pressurization device 20 is actuated (compressed). In step S20, as a result of the actuation of the movable part 20a of the pressurization device 20, the inner valve portion 21 automatically slides from the first position to the second position, thus changing the locations of the first flow passage 23 and the second flow passage 24. In step S30, pressurized fluid is provided to the hollow tubular member 11 as a result of the actuation of the movable part 20a. In step S40, the clog is cleared as a result of the actuation of the movable part 20a causing the inner valve portion 21 to move and causing the supply of pressurized fluid into the suction passage of the surgical instrument. The suction from the suction source 6 does not need to be stopped during the de-clog process. Instead, the suction is merely blocked briefly until the inner valve portion 21 moves back from the second position to the first position. Accordingly, the disclosed system is easy to construct and use.

The embodiments described, above are advantageous because they are very easy for the surgeon to use. In particular, the surgeon needs to perform a single operation (squeeze the inflation bulb, press the plunger, or turn (or similarly actuate, depending on the flow control mechanism) the compressed air cylinder) in order to change the flow path (suction or pressure) attached to the surgical instrument's suction passage and to supply the pressure. The inflation bulb embodiment is especially convenient because it automatically re-sets itself when the surgeon releases the bulb. Clogs are removed without having to withdraw the surgical instrument from the surgical site. Further, the inflation bulb embodiments are advantageous because inflation bulbs are intuitive to use, ergonomic and can be operated with a single hand.

Figure 9:
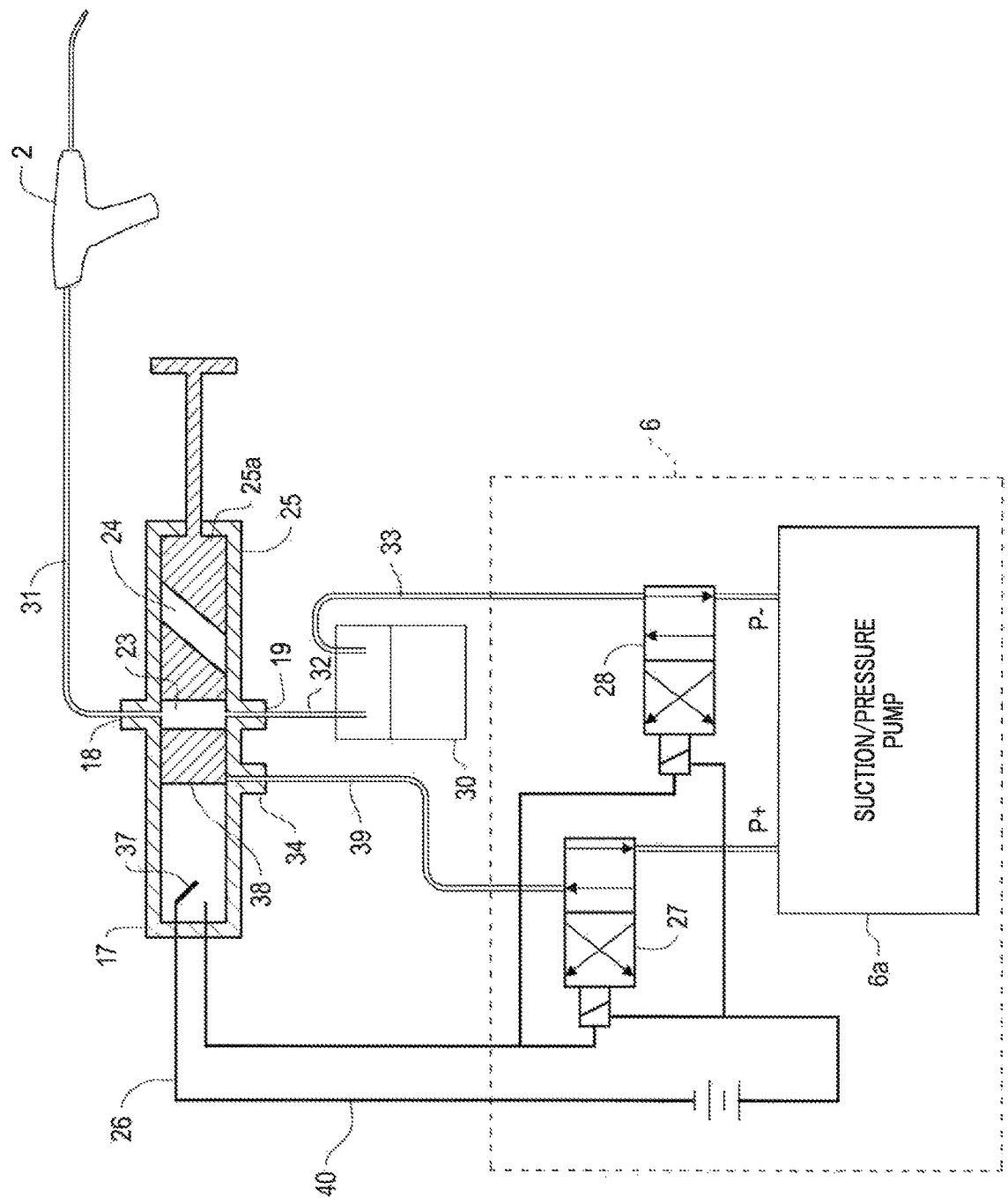
FIG. 9 illustrates a pressurization unit in a suction position according to a fourth embodiment.

FIG. 9 illustrates a fourth embodiment having a switching unit 25 that is configured to switch between a suction providing state and a positive pressure providing state. The switching unit 25 illustrated in FIG. 9 is similar to the pressurization device 20 of the first embodiment except that a contact head 38 of a movable part 25*a* of the switching unit 25 switches a switch 37 to complete a circuit 26 when the movable part 25*a* is moved toward the switch 37 (to the leftmost in FIG. 9), de-clog position, to cause a suction/pressure pump 6*a* of the suction source 6 to switch from providing suction to providing positive pressure. This is accomplished by selectively energizing and de-energizing solenoid valves 27 and 28. FIG. 9 illustrates a de-energized position in which suction is provided from the suction/pressure pump 6*a* through the switching unit 25 and to the hollow tubular member 11 of the handpiece 2. Thus, according to the fourth embodiment, a single movement of the movable part 25*a* causes the suction source 6 to switch from providing suction to providing positive pressure.

In addition to the second suction tube 32, the fourth embodiment includes a pressure tube 39 and an electrical communication cord 40 that are attached to the pressurization unit 9 (the switching unit 25 and the pump). A pump 6*a* may be used as part of the suction source 6. For many common pumps, there is a +P and a −P outlet as the pump mechanism brings in ambient air through the −P side and expels the air through the +P side. The fourth embodiment takes advantage of both sides of the pump, whereas alternative embodiments may only connect to the −P side. When the switch 37 is an open position (sec FIG. 9), the solenoid valve 27 is closed such that no air passes through the solenoid valve 27 whereas solenoid valve 28 is open to allow suction through solenoid valve 28. When the switch 37 is closed (see FIG. 10), the solenoid valves 27 and 28 are moved so as to allow pressurized air to flow through solenoid valve 27 whereas no suction flows through solenoid valve 28. The solenoid valves 27 and 28 and the pump 6*a* may be provided in a portable housing, which can include its own power source or may include a plug for obtaining power from an electrical outlet. Suction tubing from the collection canister 30, the third suction tube 33, the pressure tube 39 and the electrical communication cord plug 40 may enter into the pump housing of the suction source 6. As an alternative to the single pump 6*a* illustrated in FIGS. 9 and 10, two pumps, one using only the +P side and the other using only the −P side, may be provided. This prevents cross contamination of air from past patients that may be contained inside a singular pump and recirculated to a patient in a subsequent surgery during a positive pressurization de-clog cycle.

Figure 10:
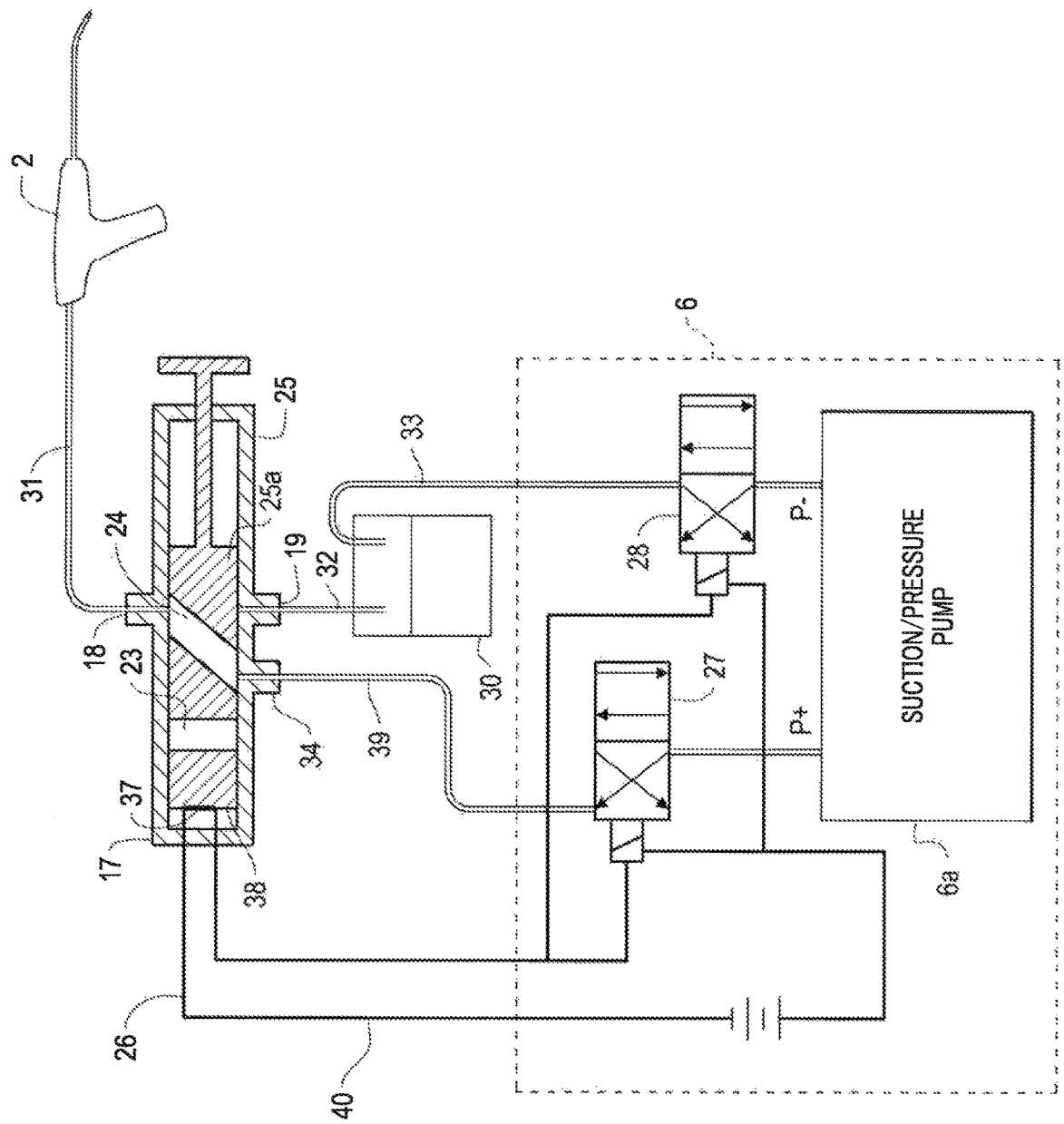
FIG. 10 illustrates the pressurization unit according to the fourth embodiment while in a de-clog position.

FIG. 10 illustrates the fourth embodiment in an energized position in which the movable part 25*a* is depressed causing the first flow passage 23 to be switched to the second flow passage 24 while at the same time causing the contact head 38 to close the switch 37 and causing the completion of the circuit 26. This causes activation of the solenoid valves 27 and 28, which results in positive pressure being provided from a positive pressure providing port of the suction/pressure pump 6*a* through the pressure tube 39 the second flow passage 24 of switching unit 25 and the first suction tube 31 to the handpiece 2 to clear a clog.

Figure 12:
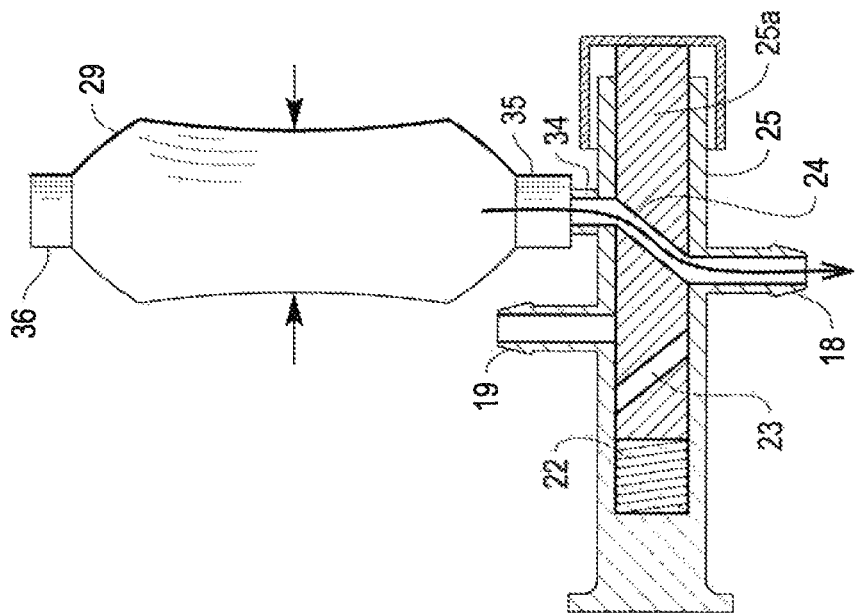
FIG. 12 illustrates the pressurization unit according to the fifth embodiment while in a de-clog position.
Figure 11:
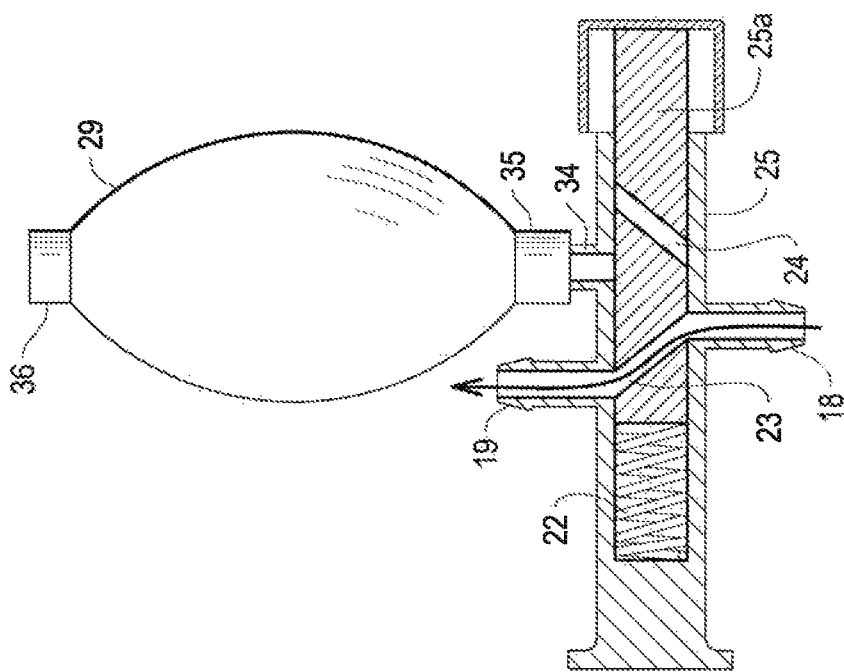
FIG. 11 illustrates a pressurization unit in a suction position according to a fifth embodiment.

FIGS. 11 and 12 illustrate a fifth embodiment having a switching unit 25 that is similar to that illustrated in the fourth embodiment except that, instead of providing positive pressure via a positive pressure providing port of the suction/pressure pump 6*a*, a manually compressible inflation bulb 29 is provided. After the movable part 25*a* is depressed in FIG. 12, pressurized fluid can be provided through the second flow passage 24 to the handpiece 2 by compressing the manually compressible inflation bulb 29. A syringe or compressed air cylinder could alternatively be used in the embodiment illustrated in FIGS. 11 and 12 instead of the manually compressible inflation bulb 29. The fourth and fifth embodiments are different from the first, second and third embodiments in that, in the fourth and fifth embodiments, the movement of the inner valve portion 21 of the switch unit 25 is not caused by the positive fluid pressure.

Figure 16A:
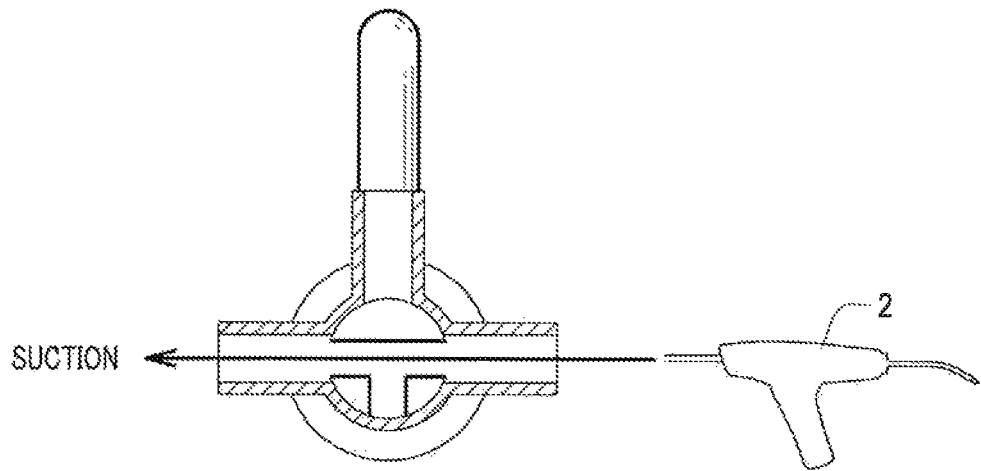
FIGS. 16a-16b illustrate an embodiment where a rotary switch switches between providing suction and providing a positive pressure.
Figure 16B:
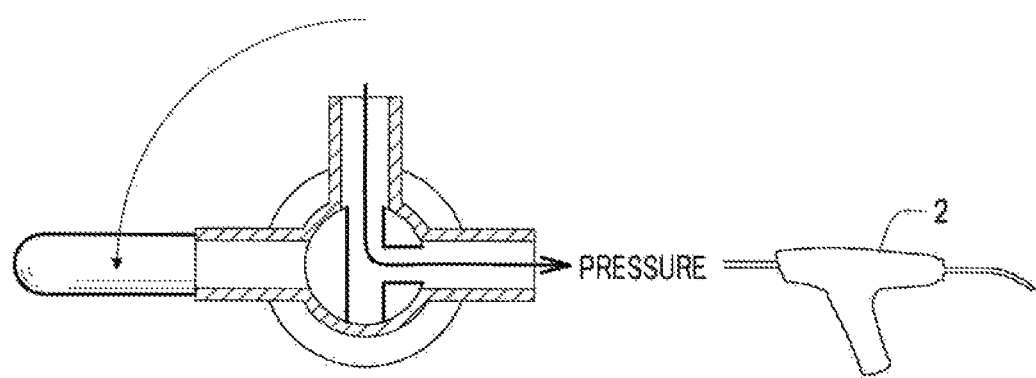

The fourth and fifth embodiments illustrated in FIGS. 9-12 utilize a trumpet style valve for the switching unit 25 to switch between providing suction and positive pressure. Instead of a trumpet style valve, various other types of switching devices may be used for the switching unit 25. For example, FIGS. 13 and 14 illustrate a switching unit 25 that is different than a trumpet valve. In particular, the switching unit 25 may be a rotary switch, a rocker switch or a sliding switch. FIGS. 15*a*-15*d* illustrate a rocker switch and a sliding switch. FIG. 15*a* illustrates a suction providing state of the rocker switch. FIG. 15*b* illustrates a de-clog providing state of the rocker switch. FIGS. 15*c*-15*d* illustrate a slider switch that can slide to selectively provide suction or allow positive pressure therethrough. FIGS. 16*a* and 16*b* illustrate different states of a rotary switch.

Figure 17:
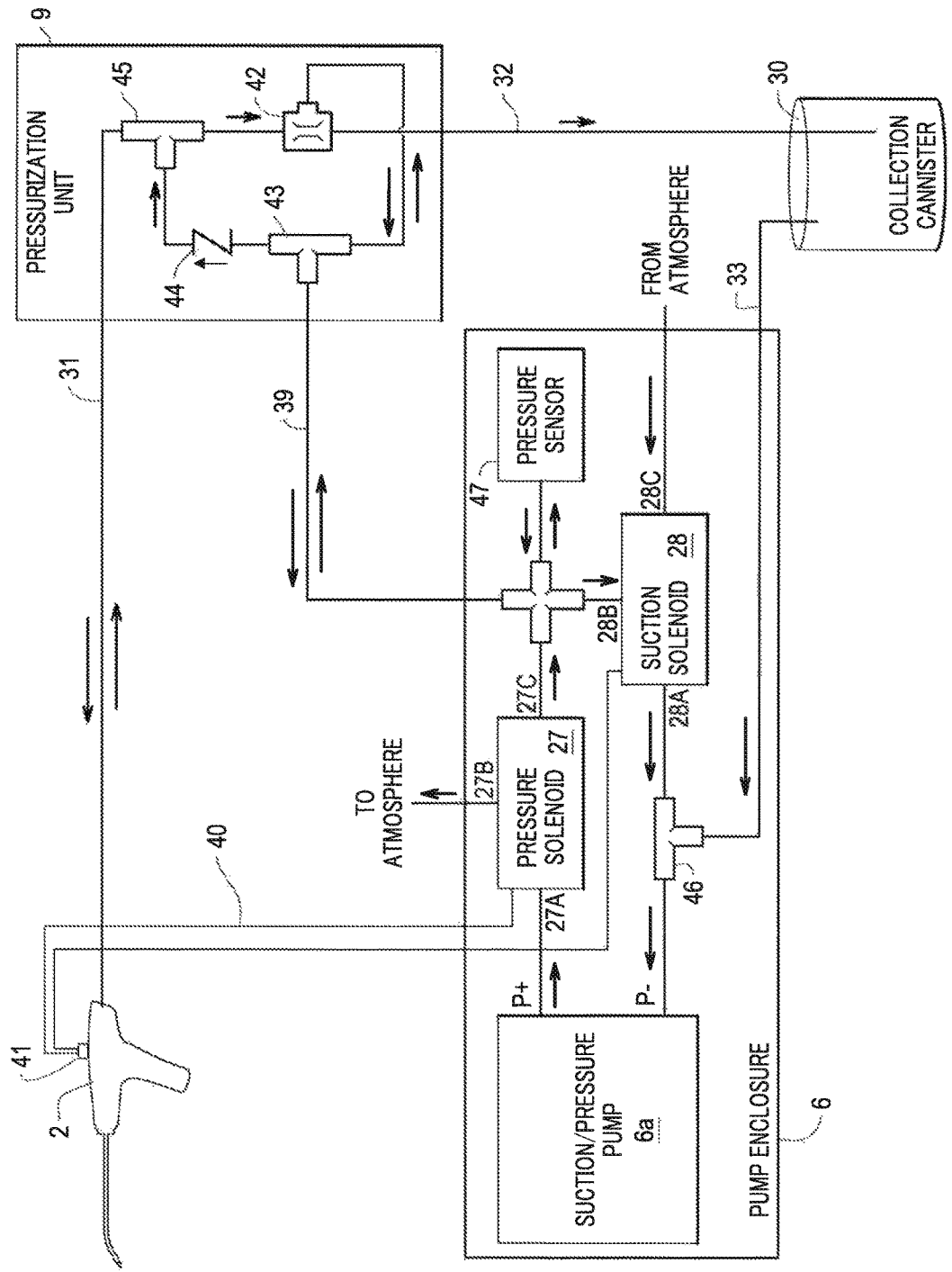
FIG. 17 illustrates a pressurization unit according to a sixth embodiment.
Figure 18:
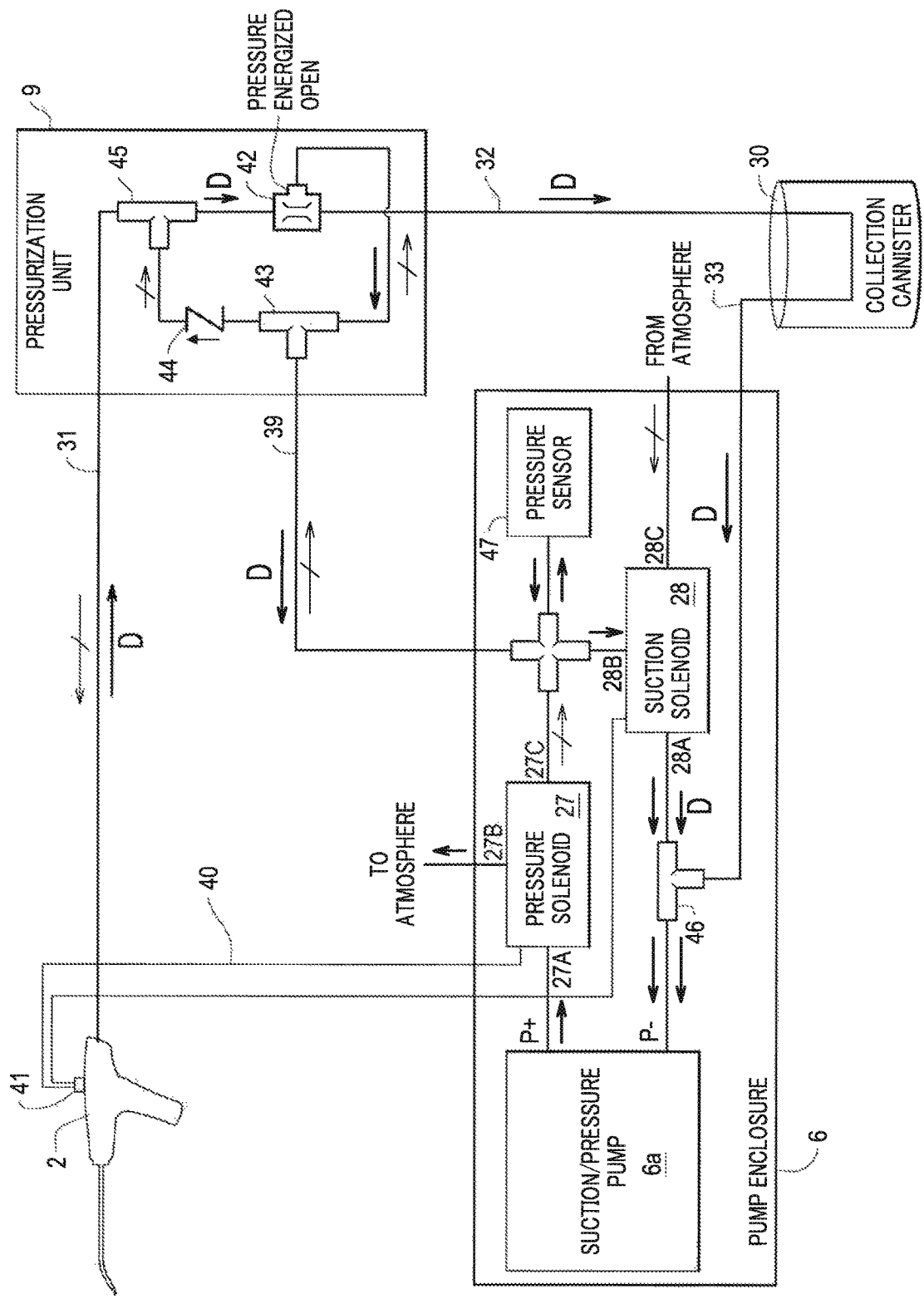
FIG. 18 illustrates the pressurization unit according to the sixth embodiment while in a suction providing state.
Figure 19:
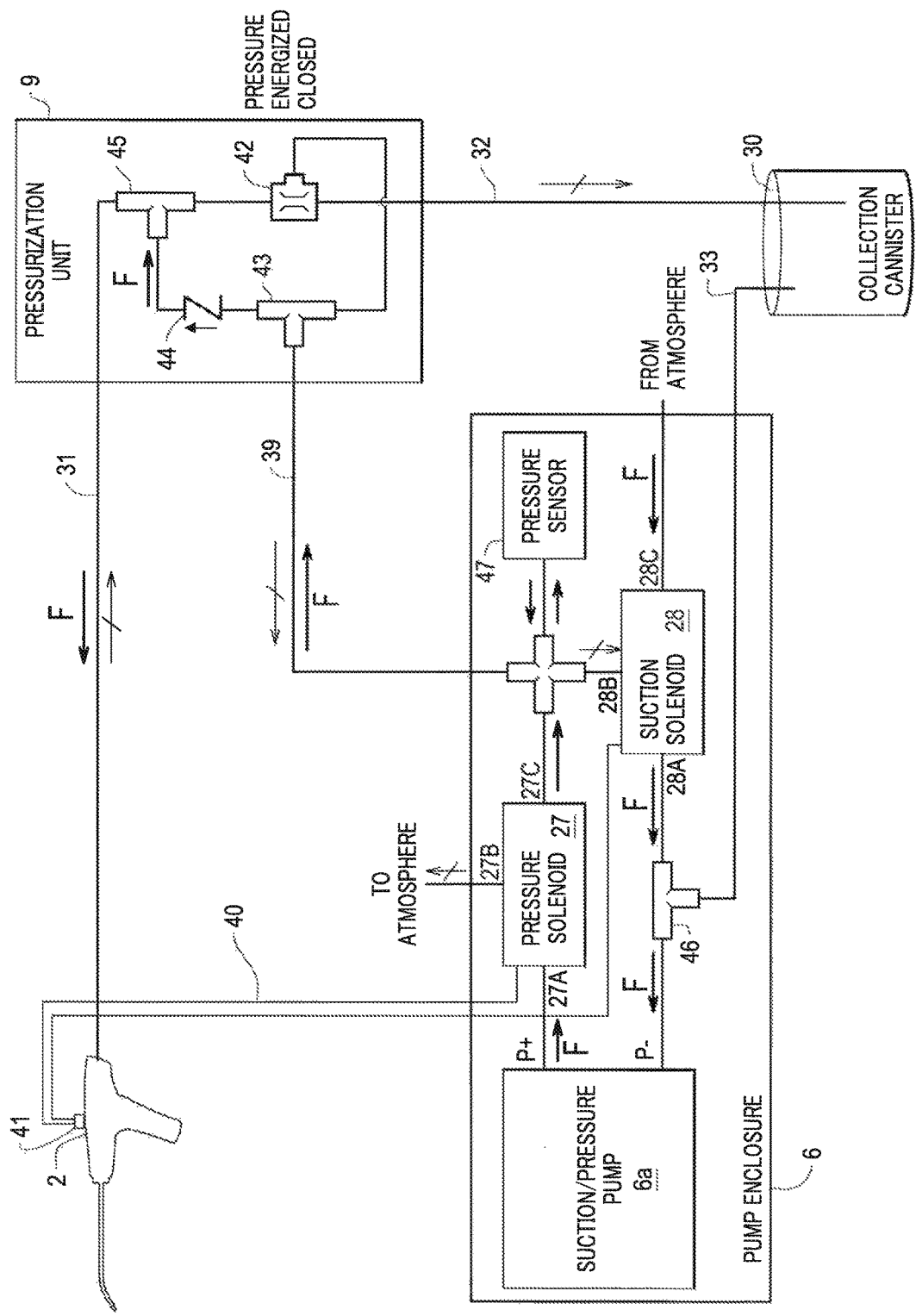
FIG. 19 illustrates the pressurization unit according to the sixth embodiment while in a positive pressure providing (de-clog) state.

FIG. 17 illustrates a sixth embodiment in which a de-clog button 41 is provided on the handpiece 2 or in the handpiece power cable 5. Different from the previous embodiments, the pressurization unit 9 of the sixth embodiment includes a de-clog valve 42, a first T-junction 43, a one way check valve 44 and a second T-junction 45. The suction source 6 of the sixth embodiment includes a suction/pressure pump 6*a*, a third T-junction 46, solenoid valves 27 and 28 and a pressure sensor 47. When the system is aspirating tissue normally (without a clog), it typically does so under a normal range of suction pressure (typically around 50% of full vacuum). When the aspiration pathway develops a clog, the pressure will climb to a much higher pressure, as the suction builds and approaches the limits of its vacuum pressure capability. This 'clog pressure' could be automatically sensed by the pressure sensor 47 in the system to initiate a de-clog action without manual intervention. FIGS. 18 and 19 respectively illustrate the operation of the sixth embodiment in an aspiration mode (suction providing) and a de-clog mode (pressure providing).

FIG. 18 illustrates the sixth embodiment in the suction providing or aspiration mode. The arrows D illustrate the flow path of the suction. As seen in FIG. 18, the de-clog valve 42 is open such that suction is provided from the suction/pressure pump 6*a* through the pressurization unit 9 and to the handpiece 2. In FIG. 18, negative pressure provided through pressure tube 39 causes the de-clog valve 42 to be in an open state. The outlet 27C of solenoid valve 27 is closed and pressurized air exits the solenoid valve 27 to the atmosphere (ATM) through outlet 27B. The inlet 28B of the solenoid valve 28 is open and suction is provided through outlet 28A and inlet 28B of the solenoid valve 28.

FIG. 19 illustrates the sixth embodiment in a de-clog or pressure providing mode. The arrows F illustrate a flow path of the positive pressure. When the de-clog button 41 is depressed, the solenoid valves 27 and 28 switch from the configurations illustrated in FIG. 18 to the configurations illustrated in FIG. 19. This results in positive pressure being supplied through the pressure tube 39 to the pressurization unit 9. The positive pressure in the pressurization unit 9 causes the de-clog valve 42 to close and causes the positive pressure to be provided through 'T'-junctions 3 and 45 to the first suction tube 31 and to the handpiece 2 to clear a clog. The de-clog valve 42 can include a pressure cuff that surrounds suction tubing. When positive pressure is supplied to the pressure cuff as in FIG. 19, the pressure cuff pinches the suction tubing so that the suction tubing is blocked.

FIG. 20a-c illustrates another embodiment of the pressurization unit. The pressurization unit 109 includes an outer valve portion 11 7 that has a first port 118 that connects to the handpiece, a second port 119 that connects to a suction source 6, and a third port 134 that connects to a pressurization device 20a. The pressurization unit 109 includes an inner valve portion 121 that is slidable between a first position and a second position. In this illustrated example, the inner valve portion 121 is slidable in a linear direction between the first position and the second position. The inner valve portion 121 may be biased toward the .first position preferably by a means of a spring 122.

When the inner valve portion 121 is in the first position (illustrated in FIG. 20a) a first flow passage 150 is created between the exterior of the inner valve portion 121 and the interior of the outer valve portion 117 that fluidically connects the first port 118 to the second port 119. Suction is provided to the hollow tubular member 11 via the first port 118, the first flow passage 150 and the second port 119.

When the inner valve portion 121 is in the second position (illustrated in FIG. 20c) a second flow passage 152 is created between the exterior of the inner valve portion 121 and the interior of the outer valve portion 117 that fluidically connects the first port 118 to the third port 134. Pressurized fluid is provided to the hollow tubular member 11 via the first port 118, the second flow passage 152 and the third port 134.

There is a sealing system 160 which fluidically isolates the second port 119 from the third port 134 when the inner valve portion 121 is in the first position and second position. The sealing system 160 may comprise a first compliable sealing member 162 which rests in a first groove 172 around the periphery of the inner valve member and a second compliable sealing member 164 which rests in a second groove 174 around the periphery of the inner valve member. The first compliable sealing member and second compliable sealing members may be compressed between the inner valve portion and the outer valve portion to create a fluidic seal therebetween. The first and second compliable sealing member 162, 164 may be o-rings.

As illustrated in FIG. 20a when the inner valve portion 121 is in the first position the first compliable sealing 162 member fluidically isolates the third port 134 from the first port 118, first flow passage 150, and second port 119. When the inner valve portion 121 is in the second position the second compliable sealing member 164 fluidically isolates the second port 119 from the first port 118, the second flow path 152, and the third port 134.

The sealing system 160 may also fluidically isolate the second port 119 from the third port 134 when the inner valve portion 121 is in any position between the first and second position. FIG. 20b shows the inner valve member 121 in an intermediate position. In this intermediate position, the inner valve portion 121 has started to move from the first position to the second position. The second compliable sealing 164 member has sealed the gap between the inner valve portion 121 and the outer valve portion 117 to fluidically isolate the second port 119 from the first port 118 while the first compliable member 162 is still sealing the gap between the inner valve portion 121 and the outer valve 117 to isolate the third port 134 from the first port 118.

FIG. 21a-c illustrates another embodiment of the pressurization unit 209. The pressurization unit 209 includes an outer valve portion 217 that has a first port 218 that connects to the handpiece 2, a second port 219 that connects to a suction source 6, and a third port 234 that connects to a pressurization device 20a. The pressurization unit 209 includes an inner valve portion 221 that is slidable between a first position and a second position. In this illustrated example, the inner valve portion 221 is slidable in a linear direction L between the first position and the second position. The inner valve portion 221 may be biased toward the first position preferably by a means of a spring 222.

The inner valve portion 221 includes a first flow passage 223. The first flow passage 223 may be a bore through the inner valve portion 221. When the inner valve portion 221 is in the first position (illustrated in FIG. 21a) first flow passage 223 fluidically connects the first port 218 to the second port 219. Suction is provided to the hollow tubular member 11 via the first port 218, the first flow passage 223 and the second port 219. The bore may be any shape that fluidically connects the first port 218 to the second port 219 when the inner valve member 221 is in the first position so that suction can be maintained from the suction source 6 through the first flow passage 223 to the hollow tubular member 11. The first port 218 and second port 219 may be in line with each other. The first flow passage 223 can be a straight bore through the inner valve portion 221 that is configured to be in line with the first and second port 218, 219 when the inner valve portion 221 is in the first position, so that the first flow passage 223 may form a suction pathway that has few or no curves, bends, corners, or transitions. Or first port 218 and second port 219 may not be in line with each other and the first flow passage 223 may be a straight bore through the inner valve portion 221 that is configured to be in line with either the first or second port 218, 219 when the inner valve portion 221 is in the first position. The pressurization system can be used on surgical cutters or other surgical devices that may draw blood, fluids, or pieces of cut tissue away from the cutting tool to the suction canister. A straight suction path having few or no transitions may facilitate collection of the cut tissue without blockage.

As seen in FIG. 21c, when the inner valve portion 221 is in the second position a second flow passage 252 is created between the exterior of the inner valve portion 221 and the interior of the outer valve portion 217 that fluidically connects the first port 218 to the third port 234. Pressurized fluid is provided to the hollow tubular member 11 via the first port 218, the second flow passage 252 and the third port 234.

There is a sealing system 260 which fluidically isolates the second port 219 from the third port 234 when the inner valve portion 221 is in the first position and second position. The sealing system 260 may comprise a first compliable sealing member 262 which rests in a first groove 272 around the periphery of the inner valve member and a second compliable sealing member 264 which rests in a second groove 274 around the periphery of the inner valve member. The first compliable sealing member 262 and second compliable sealing member 264 may be o-rings.

As illustrated in FIG. 21a when the inner valve portion 221 is in the first position the first compliable sealing member 262 may fluidically isolate the third port 234 from the first port 218, first flow passage 223, and second port 219. When the inner valve portion 221 is in the first position, the second compliable sealing member 262 may provide a second, redundant, seal that fluidically isolates the third port 234 from the first port 218, first flow passage 223, and second port 219. As illustrated in FIG. 21c, when the inner valve portion 221 is in the second position the second compliable sealing member 264 fluidically isolates the second port 219 from the first port 218, the second flow path 252, and the third port 234.

The sealing system 260 may also fluidically isolate the second port 219 from the third port 234 when the inner valve portion 221 is in any position between the first and second position. FIG. 21b shows the inner valve member in an intermediate position. In this intermediate position, the inner valve portion 221 has started to move from the first position to the second position. The second compliable sealing member 264 has sealed the gap between the inner valve portion 221 and the outer valve portion 217 to isolate the second port 219 from the first port 218 while the first compliable 262 member is still sealing the gap between the inner valve member 221 and the outer valve member 217 to isolate the third port 234 from the first port 218.

In the embodiment in FIG. 21a-c, the first and second ports 218, 219 are in line. The first and second compliable members 262, 264 may be angled reduce the amount of travel of the inner valve portion 221 from the first position to the second position. Reducing the amount of travel of the inner valve portion 221 may reduce the total size of the pressurization unit 209. The first groove 272, and thereby the first compliable sealing member 262, may be inclined at a first angle 282 to a plane P that is perpendicular to the direction of travel L of the inner valve portion 221 from the first position to the second position. The second groove 274, and thereby the second compliable sealing member 264, may be inclined at a second angle 284 to the plane P that is perpendicular to the direction of travel L of the inner valve portion 221 from the first position to the second position. The first angle and the second angle 282, 284 may be equal so that the first and second grooves 272, 274, and thereby the first and second compliable sealing members 262, 264, are parallel. Alternatively, the first angle and second angles 282, 284 may be different so that the first and second grooves 272, 274, and thereby the first and second compliable sealing members 262, 264, are not parallel.

There may be a spring 222, such as a helical coil spring, to bias the inner valve portion 221 towards the first position. The spring 222 may be configured to provide a biasing force between the outer valve portion 217 and the inner valve position 221. The spring 222 may be located in a cavity 224 at the end 225 of the outer valve portion 217. There may be a compliable sealing member 266 between the inner valve portion 221 and the outer valve portion 217 to fluidically isolate the spring 222 and the spring cavity 224 from the first port 218, second port 219, third port 234, first flow passage 223, second flow passage 252, or preferably all. The pressurization system can be used on surgical cutters or other surgical devices that may draw blood, fluids, or pieces of cut tissue away from the cutting tool to the suction canister. A suction pathway and irrigation pathway isolated from a biasing component, such as a spring, may facilitate collection of the cut tissue or irrigation without blockage.

FIGS. 22a-b illustrate another embodiment of the pressurization unit. The pressurization unit 309 includes an outer valve portion 317 that has a first port 318 that connects to the handpiece, a second port 319 that connects to a suction source 6, and a third port 334 that connects to a pressurization device. The pressurization unit 309 includes an inner valve portion 321 that is rotationally slidable between a first position and a second position.

The inner valve portion 321 includes a first flow passage 323. The flow passage can be a bore through the inner valve portion 321. When the inner valve portion 321 is in the first position (illustrated in FIG. 22a) first flow passage 323 fluidically connects the first port 318 to the second port 319. Suction is provided to the hollow tubular member 11 via the first port 318, the first flow passage 323 and the second port 319. The bore can be any shape that fluidically connects the first port 318 to the third port 334 when the inner valve member 321 is in the first position so that suction can be maintained from the suction source 6 through the first flow passage 323 to the hollow tubular member 11. The first port 318 and second port 319 can be in line with each other. The first flow passage 323 can be a straight bore through the inner valve portion 321 that is configured to be in line with the first and second ports 318, 319 when the inner valve portion 321 is in the first position, so that a suction pathway may be formed that has few, or no, curves, bends, corners, or transitions.

As illustrated in FIG. 22b, when the inner valve portion 321 is in the second position a second flow passage 352 is created between the exterior of the inner valve portion 321 and the interior of the outer valve portion 317 that fluidically connects the first port 318 to the third port 334. Pressurized fluid is provided to the hollow tubular member 11 via the first port 318, the second flow passage 352 and the third port 334.

There may be a sealing system 360 which fluidically isolates the second port 319 from the third port 334 when the inner valve portion 321 is in the first position and second position. The sealing system 360 may comprise a first compliable sealing member 362 Which rests in a first groove 372 around the periphery of the inner valve member and a second compliable sealing member 364 which rests in a second groove 374 around the periphery of the inner valve member, and seals the gap between the inner valve portion 321 and the outer valve portion 317. The first compliable sealing member 362 and second compliable sealing member 364 may be o-rings.

As illustrated in FIG. 22a, when the inner valve portion 321 is in the first position the first compliable sealing member 362 fluidically isolates the third port 334 from the first port, first flow passage 323, and second port 319. When the inner valve portion 321 is in the second position the second compliable sealing member 364 fluidically isolates the second port 319 from the first port, the second flow path, and the third port 334.

When the movable part 20a of the pressurization device 20 is compressed, positive pressure emitted from the inflation bulb into a passage at the third port 334 causes the inner valve portion 321 to slidably rotate in a direction toward pressure flow within the outer valve portion 317 to move the inner valve portion 321 from the first position to the second position. This causes the positive pressure emitted from the inflation bulb to pass in the direction. of the second flow passage 324, out the first port 318 and to the hollow tubular member 1.

These illustrative examples disclose that a pressurization unit may able be used to provide de-clog capabilities to surgical cutting instruments. The pressurization unit may also be used to provide irrigation and suction to other surgical devices that may require both irrigation and suction; such as lavage apparatuses, ventilator lumens, endoscope cleaners, and such. Examples of some surgical devices may be found in U.S. Pat. Nos. 5,439,022 and 7,270,647; and U.S. Patent Application Publication Nos. 2006/0264995 and 2013/0289595 all of which are incorporated by reference herein for all purposes.

What has been described and illustrated herein are preferred embodiments of the invention along with some variations. The terms, descriptions and figures used herein are set forth by way of illustration only and are not meant as limitations. Those skilled in the art will recognize that many variations are possible within the spirit and scope of the invention.

What is claimed is:

1. A surgical instrument comprising:
a hollow tubular member having a distal end;
a handpiece connected to a proximal end of the hollow tubular member and having a suction passage in fluid connection with the hollow tubular member;
a suction pump that is configured to produce suction at the distal end of the hollow tubular member; and
a pressurization unit provided between the suction passage and the suction pump, the pressurization unit comprising:
an outer valve portion having a first port connected to the suction passage, a second port connected to the suction pump, and a third port;
a pressurization device connected to the third port, the pressurization device having a movable part that is configured to generate pressurized fluid when the movable part is moved; and
an inner valve portion that is slidably provided within the outer valve portion, the inner valve portion including a first flow passage that is a bore which passes through the inner valve portion, the first flow passage fluidically connecting the first port and the second port of the outer valve portion to each other when the inner valve portion is in a first position,
the inner valve portion configured to move from the first position to a second position to create a second flow passage that passes between an exterior surface of the inner valve portion and an interior surface of the outer valve portion to fluidically connect the first port and the third port of the outer valve portion to each other when the inner valve portion is in the second position, the second passage does not pass through the inner valve portion;
wherein the pressurization unit is configured such that the pressurized fluid from the pressurization device causes the inner valve portion to move from the first position to the second position, thereby providing positive pressure to the hollow tubular member.

2. The surgical instrument according to claim 1 further comprising:
a seal system that fluidically seals the second port from the third port when the inner valve member is in the first position and when the inner valve member is in the second position.

3. The surgical instrument according to claim 2, wherein the seal system fluidically seals the second port from the third port when the inner valve portion is in any position between the first position and the second position.

4. The surgical instrument according to claim 3, wherein the seal system comprises:
a first compliable seal member configured to produce a fluidic seal between the second port and the third port when the inner valve portion is in the first position, and
a second compliable seal member configured to produce a fluidic seal between the second port and the third port when the inner valve portion is in the second position.

5. The surgical instrument according to claim 4, wherein the inner valve portion is configured to move from the first position to the second position in a direction of slidable movement that is linear, and the seal system further comprises:
a first groove disposed around the periphery of the inner valve portion and inclined at a first angle to a plane that is perpendicular to the direction of slidable movement of the inner valve portion, the first groove configured to accept the first compliable seal member, and
a second groove disposed around the periphery of the inner valve portion and inclined at a second angle to the plane that is perpendicular to the direction of slidable movement of the inner valve portion, the second groove configured to accept the second compliable seal member.

6. The surgical instrument according to claim 5, wherein the first angle and the second angle equal.

7. The surgical instrument according to claim 1, wherein the inner valve portion is biased towards the first position.

8. The surgical instrument according to claim 7, further comprising a spring that provides a biasing force to the inner valve portion to bias the inner valve portion towards the first position.

9. The surgical instrument according to claim 8, wherein a first portion of the spring is secured to the inner valve portion and a second portion of the spring is secured to the outer valve portion and the spring is fluidically isolated from the first flow passage and the second flow passage.

10. A surgical instrument comprising:
a hollow tubular member having a distal end;
a suction passage in fluid connection with the hollow tubular member;
a suction pump that is configured to produce suction at the distal end of the hollow tubular member; and
a pressurization unit provided between the suction passage and the suction pump, the pressurization unit comprising:
an outer valve portion having a first port configured to connect to the suction passage, a second port configured to connect to the suction pump and a third port;
a pressurization device configured to connect to the third port, the pressurization device having a movable part that is configured to generate pressurized fluid when the movable part is moved;
an inner valve portion that is slidably provided within the outer valve portion and that is configured to move from a first position to a second position;
a first flow passage that fluidically connects the first port and the second port of the outer valve portion to each other when the inner valve portion is in the first position;
a second flow passage that fluidically connects the first port and the third port of the outer valve portion to each other when the inner valve portion is in the second position, the second flow passage is between an exterior surface of the inner valve portion and an interior surface of the outer valve portion, the second passage does not pass through the inner valve portion;
a first compliable seal member configured to produce a fluidic seal between the second port and the third port when the inner valve portion is in the first position; and
a second compliable seal member configured to produce a fluidic seal between the second port and the third port when the inner valve portion is in the second position.

11. The surgical instrument according to claim 10, wherein the first port and the second port are in line with each other.

12. The surgical instrument according to claim 11, wherein
the first flow passage is a straight bore through the inner valve portion; and
the first flow passage is configured to be in line with the first port and the second port when the inner valve portion is in the first position.

13. The surgical instrument according to claim 12, wherein
the inner valve portion is configured to move from the first position to the second position in a direction of slidable movement that is linear, and
the inner valve portion comprising:
a first groove disposed around the periphery of the inner valve portion and inclined at a first angle to a plane that is perpendicular to the direction of slidable movement of the inner valve portion, the first groove configured to accept the first compliable seal member, and
a second groove disposed around the periphery of the inner valve portion and inclined at a second angle to the plane that is perpendicular to the direction of slidable movement of the inner valve portion, the second groove configured to accept the second compliable seal member.

14. A surgical instrument comprising:
a hollow tubular member having a distal end;
a handpiece connected to a proximal end of the hollow tubular member and having a suction passage in fluid connection with the hollow tubular member;
a suction pump that is configured to produce suction at the distal end of the tubular member;
a pressurization unit provided between the suction passage and the suction pump, the pressurization unit comprising:
an outer valve portion having:
a first port connected to the suction passage,
a second port connected to the suction pump, the first port and the second port are in line with each other, and
a third port;
a pressurization device connected to the third port, the pressurization device having a movable part that is configured to generate pressurized fluid when the movable part is moved;
an inner valve portion that is slidably provided within the outer valve portion and that is configured to move from a first position to a second position, the inner valve portion including:
a first flow passage that passes through the inner value portion, the first flow passage fluidically connecting the first port and the second port of the outer valve portion to each other when the inner valve portion is in the first position, the first flow passage being a straight bore through the inner valve portion that is configured to be in line with the first port and the second port when the inner valve portion is in the first position, and
a second flow passage that passes between an exterior surface of the inner valve portion and an interior surface of the outer valve portion to fluidically connect the first port and the third port of the outer valve portion to each other when the inner valve portion is in the second position, the second passage does not pass through the inner valve portion; and
a seal system that fluidically seals the second port from the third port when the inner valve member is in the first position, when the inner valve member is in the second position, and when the inner valve portion is in any position between the first position and the second position;
wherein the pressurization unit is configured such that the pressurized fluid from the pressurization device causes the inner valve portion to move from the first position to the second position, thereby providing positive pressure to the hollow tubular member.

15. The surgical instrument according to claim 14, wherein
the inner valve portion is configured to move from the first position to the second position in a direction of slidable movement that is linear, and
the seal system comprises:
a first groove disposed around the periphery of the inner valve portion and inclined at a first angle to a plane that is perpendicular to the direction of slidable movement of the inner valve portion, the first groove configured to accept a first compliable seal member, the first compliable seal member configured to produce a fluidic seal between the second port and the third port when the inner valve portion is in the first position, and
a second groove disposed around the periphery of the inner valve portion inclined at a second angle to the plane that is perpendicular to the direction of slidable movement of the inner valve portion, the second groove configured to accept a second compliable seal member the second compliable seal member configured to produce a fluidic seal between the second port and the third port when the inner valve portion is in the second position.

16. The surgical instrument according to claim 14, further comprising:
a spring within the outer valve portion and that provides a biasing force to bias the inner valve portion towards the first position, a first portion of the spring secured to the inner valve portion and a second portion of the spring secured to the outer valve portion, the spring being fluidically isolated from the first flow passage and the second flow passage.

* * * * *